(12) United States Patent
Berns et al.

(10) Patent No.: US 11,026,473 B2
(45) Date of Patent: Jun. 8, 2021

(54) FOOT SUPPORT ARTICLE

(71) Applicant: Under Armour, Inc., Baltimore, MD (US)

(72) Inventors: Jason A. Berns, Montclair, NJ (US); Alan Guyan, Baltimore, MD (US); Justin Schlothhauer, Baltimore, MD (US); Kevin Fisher, Baltimore, MD (US); Michael White, Baltimore, MD (US)

(73) Assignee: Under Armour, Inc., Baltimore, MD (US)

( * ) Notice: Subject to any disclaimer, the term of this patent is extended or adjusted under 35 U.S.C. 154(b) by 144 days.

(21) Appl. No.: 15/619,894

(22) Filed: Jun. 12, 2017

(65) Prior Publication Data

US 2017/0273814 A1    Sep. 28, 2017

Related U.S. Application Data

(60) Continuation of application No. 14/013,684, filed on Aug. 29, 2013, now Pat. No. 9,707,119, which is a division of application No. 13/157,023, filed on Jun. 9, 2011, now Pat. No. 9,402,437, which is a continuation-in-part of application No. 13/111,704, filed on May 19, 2011, now abandoned.

(51) Int. Cl.
| | | |
|---|---|---|
| *A43B 7/14* | (2006.01) | |
| *A43B 7/20* | (2006.01) | |
| *A43C 1/00* | (2006.01) | |
| *A43C 11/14* | (2006.01) | |

(52) U.S. Cl.
CPC ................. *A43B 7/14* (2013.01); *A43B 7/20* (2013.01); *A43C 1/003* (2013.01); *A43C 11/14* (2013.01); *A43C 11/1493* (2013.01)

(58) Field of Classification Search
CPC ........ A61F 5/011; A61F 5/027; A61F 13/066; A61F 13/62; A61F 13/622; A43B 7/14; A43B 7/20; A43B 7/1495; A43B 7/18; A43B 23/0265; A43C 1/003; A43C 11/1493; A43C 11/14
USPC ........................................... 36/117.1
See application file for complete search history.

(56) References Cited

U.S. PATENT DOCUMENTS

| | | |
|---|---|---|
| 325,280 A | 9/1885 | Smadbeck et al. |
| 1,205,206 A | 11/1916 | Hofmeister |
| (Continued) | | |

FOREIGN PATENT DOCUMENTS

| | | |
|---|---|---|
| WO | 8910731 | 11/1989 |
| WO | 9831247 | 7/1998 |
| WO | 2009112814 | 9/2009 |

*Primary Examiner* — Heather Mangine
(74) *Attorney, Agent, or Firm* — Maginot, Moore & Beck LLP

(57) ABSTRACT

An article of footwear includes a sole, an upper defining a foot cavity, and a brace member. The brace member is comprised of a non-elastic resilient material. The brace member is positioned within a pocket in the upper and extends from a heel portion to above an ankle portion of the upper. The brace member may be provided with a top plate member and a base plate member with a central shaft extending between the top plate member and the base plate member. The central shaft may have a C-shape that curves around an ankle of a human foot positioned within the foot cavity.

18 Claims, 26 Drawing Sheets

(56) References Cited

U.S. PATENT DOCUMENTS

| | | | | |
|---|---|---|---|---|
| 1,649,173 A * | 11/1927 | McDonough | A43B 7/1495 | 36/170 |
| 1,717,432 A | 6/1929 | Botti | | |
| 2,531,763 A | 11/1950 | Andre | | |
| 3,073,305 A * | 1/1963 | Biggs, Jr. | A61F 5/0111 | 602/65 |
| 3,234,667 A * | 2/1966 | Bovay | A43B 5/02 | 36/105 |
| 3,334,898 A * | 8/1967 | McCrory | A63B 21/065 | 36/132 |
| 3,674,023 A * | 7/1972 | Mann | A61F 13/066 | 128/DIG. 15 |
| 3,680,549 A | 8/1972 | Lehneis | | |
| 3,813,796 A * | 6/1974 | Olivieri | A43C 11/1413 | 36/117.1 |
| 4,280,286 A * | 7/1981 | Sartor | A43B 5/0427 | 36/105 |
| 4,313,433 A * | 2/1982 | Cramer | A43B 7/1495 | 602/27 |
| 4,366,634 A | 1/1983 | Giese et al. | | |
| 4,441,265 A * | 4/1984 | Burns | A43B 5/00 | 36/114 |
| 4,476,639 A * | 10/1984 | Zaccaria | A43B 5/00 | 36/114 |
| 4,523,392 A * | 6/1985 | Gabrielli | A43B 5/0405 | 36/10 |
| D280,567 S | 9/1985 | Ji | | |
| 4,551,932 A * | 11/1985 | Schoch | A43C 11/16 | 36/117.1 |
| 4,621,648 A * | 11/1986 | Ivany | A43B 5/00 | 36/89 |
| 4,640,025 A * | 2/1987 | DeRenzo | A43C 11/1493 | 36/114 |
| 4,649,939 A * | 3/1987 | Curtis | A61F 5/0104 | 602/27 |
| 4,662,088 A | 5/1987 | Autry | | |
| 4,724,847 A | 2/1988 | Nelson | | |
| 4,727,863 A | 3/1988 | Nelson | | |
| 4,771,768 A | 9/1988 | Crispin | | |
| 4,794,674 A * | 1/1989 | Mintel | A43C 11/14 | 24/712.1 |
| 4,811,498 A * | 3/1989 | Barret | A43B 7/1495 | 36/117.2 |
| 4,825,856 A | 5/1989 | Nelson | | |
| 4,864,741 A * | 9/1989 | Beauchemin | A43B 7/1495 | 2/239 |
| 4,869,267 A * | 9/1989 | Grim | A43B 7/20 | 602/27 |
| 4,878,504 A * | 11/1989 | Nelson | A61F 13/066 | 602/27 |
| 4,922,630 A * | 5/1990 | Robinson | A43B 5/00 | 36/89 |
| 5,016,623 A * | 5/1991 | Krahenbuhl | A61F 13/066 | 128/882 |
| 5,031,340 A * | 7/1991 | Hilgarth | A43B 5/0427 | 36/117.1 |
| 5,038,762 A | 8/1991 | Hess | | |
| 5,067,486 A | 11/1991 | Hely | | |
| 5,090,138 A | 2/1992 | Borden | | |
| 5,113,526 A * | 5/1992 | Wang | A41D 31/245 | 2/2.5 |
| 5,226,875 A | 7/1993 | Johnson | | |
| 5,269,078 A * | 12/1993 | Cochrane | A43B 5/00 | 36/170 |
| 5,317,820 A * | 6/1994 | Bell | A43B 5/00 | 36/114 |
| 5,323,549 A * | 6/1994 | Segel | A43B 7/1495 | 36/140 |
| 5,366,439 A * | 11/1994 | Peters | A43B 7/20 | 602/13 |
| 5,400,529 A * | 3/1995 | Bell | A43B 5/00 | 36/114 |
| 5,408,761 A | 4/1995 | Gazzano | | |
| 5,472,411 A * | 12/1995 | Montag | A61F 5/0111 | 128/882 |
| 5,499,461 A | 3/1996 | Danezin | | |
| 5,606,808 A * | 3/1997 | Gilliard | A43B 5/0401 | 36/100 |
| 5,651,197 A * | 7/1997 | James | A43B 7/1495 | 36/50.1 |
| 5,669,160 A | 9/1997 | Pozzebon | | |
| 5,672,156 A * | 9/1997 | Jimenez Ramos | A43B 7/20 | 36/89 |
| 5,676,641 A * | 10/1997 | Arensdorf | A61F 5/0111 | 602/27 |
| 5,704,140 A * | 1/1998 | Fields | A43B 7/1495 | 36/132 |
| 5,711,092 A | 1/1998 | Despres | | |
| 5,755,044 A * | 5/1998 | Veylupek | A43C 1/003 | 36/50.1 |
| 5,771,608 A * | 6/1998 | Peterson | A43B 5/00 | 36/50.1 |
| 5,791,068 A * | 8/1998 | Bernier | A43B 1/0072 | 36/50.1 |
| 5,802,742 A | 9/1998 | Baude | | |
| 5,819,439 A * | 10/1998 | Sanchez | A43B 5/00 | 36/89 |
| 5,826,353 A | 10/1998 | Woznicki | | |
| 5,832,636 A | 10/1998 | Lyden | | |
| 5,865,778 A * | 2/1999 | Johnson | A43B 7/20 | 36/88 |
| 5,894,684 A | 4/1999 | Sand | | |
| 5,946,827 A | 9/1999 | Okajima | | |
| 5,951,504 A | 9/1999 | Iglesias | | |
| 5,992,057 A * | 11/1999 | Monti | A43B 5/02 | 36/50.1 |
| 6,056,312 A * | 5/2000 | Hogstedt | A63C 10/06 | 280/14.24 |
| 6,079,124 A | 6/2000 | Dalvy | | |
| 6,117,098 A * | 9/2000 | Weber | A61F 13/066 | 602/27 |
| 6,148,544 A | 11/2000 | Keen | | |
| 6,245,035 B1 | 6/2001 | Shrijver | | |
| 6,272,772 B1 * | 8/2001 | Sherman | A43B 5/16 | 36/89 |
| 6,276,708 B1 * | 8/2001 | Hogstedt | A63C 10/06 | 280/14.22 |
| 6,324,773 B1 * | 12/2001 | Gaither | A43C 1/00 | 36/50.1 |
| 6,427,362 B2 | 8/2002 | Rork | | |
| 6,442,873 B2 | 9/2002 | Rork | | |
| 6,663,583 B1 * | 12/2003 | Janis | A61F 5/0111 | 602/65 |
| 6,691,434 B1 | 2/2004 | Couturier | | |
| 6,732,455 B2 | 5/2004 | Bordin | | |
| 6,772,541 B1 * | 8/2004 | Ritter | A43B 7/14 | 36/50.1 |
| 6,793,640 B1 | 9/2004 | Avon | | |
| 6,811,540 B1 | 11/2004 | Ritchie | | |
| 6,877,257 B2 | 4/2005 | Delgorgue | | |
| 6,952,891 B2 * | 10/2005 | Hirayama | A43B 5/0405 | 36/10 |
| D512,212 S | 12/2005 | Hatfield | | |
| D512,826 S | 12/2005 | Hatfield | | |
| 7,013,586 B1 | 3/2006 | Hatfield | | |
| 7,086,181 B2 * | 8/2006 | Farys | A43B 5/002 | 36/117.6 |
| 7,094,213 B1 * | 8/2006 | Cook | A61F 13/065 | 36/140 |
| 7,171,766 B2 * | 2/2007 | Bouche | A43B 1/0081 | 36/89 |
| 7,219,444 B2 * | 5/2007 | Hall | A43B 5/0401 | 36/10 |
| 7,370,438 B2 | 5/2008 | Vattes | | |
| 7,370,442 B2 | 5/2008 | Jung | | |
| 7,380,354 B2 * | 6/2008 | Yamashita | A43B 5/00 | 36/50.1 |
| 7,618,388 B1 | 11/2009 | Chan | | |

(56) References Cited

U.S. PATENT DOCUMENTS

| | | | |
|---|---|---|---|
| 7,753,865 B1* | 7/2010 | Hely | A61F 13/065 128/882 |
| 8,307,568 B2 | 11/2012 | Bell | |
| D680,714 S | 4/2013 | Della Valle | |
| 9,713,359 B2* | 7/2017 | Ko | A43B 7/1495 |
| 9,826,795 B2* | 11/2017 | Foxen | A43B 7/20 |
| 2001/0005948 A1 | 7/2001 | Pellegrini | |
| 2001/0015023 A1 | 8/2001 | Funk | |
| 2002/0050076 A1 | 5/2002 | Borsoi | |
| 2002/0062579 A1* | 5/2002 | Caeran | A43B 5/0401 36/115 |
| 2002/0148142 A1* | 10/2002 | Oorei | A43C 1/00 36/129 |
| 2003/0079376 A1* | 5/2003 | Oorei | A43B 5/00 36/50.1 |
| 2003/0097766 A1 | 5/2003 | Morgan | |
| 2003/0115777 A1 | 6/2003 | Hall | |
| 2003/0233062 A1 | 12/2003 | McCormick | |
| 2004/0074110 A1* | 4/2004 | Borsoi | A43B 5/0405 36/50.5 |
| 2004/0078999 A1* | 4/2004 | Freed | A43C 1/003 36/50.1 |
| 2004/0205982 A1 | 10/2004 | Challe | |
| 2004/0244221 A1* | 12/2004 | Hall | A43B 5/0405 36/10 |
| 2005/0115109 A1* | 6/2005 | Goldman | A43B 7/1495 36/50.5 |
| 2005/0198869 A1* | 9/2005 | Bouche | A43B 1/0081 36/89 |
| 2005/0268493 A1* | 12/2005 | Foxen | A43B 3/242 36/89 |
| 2006/0032090 A1* | 2/2006 | Chen | A43C 11/14 36/58.5 |
| 2006/0075661 A1 | 4/2006 | Ramsey | |
| 2006/0075663 A1 | 4/2006 | Nakano | |
| 2006/0080864 A1* | 4/2006 | Chen | A43C 11/14 36/89 |
| 2006/0084899 A1 | 4/2006 | Verkade | |
| 2006/0117606 A1* | 6/2006 | Chen | A43C 1/04 36/50.1 |
| 2006/0137226 A1 | 6/2006 | Jung | |
| 2006/0185193 A1 | 8/2006 | Pellegrini | |
| 2006/0191164 A1* | 8/2006 | Dinndorf | A43B 7/18 36/50.1 |
| 2006/0196083 A1 | 9/2006 | Martin et al. | |
| 2006/0270958 A1 | 11/2006 | George | |
| 2006/0283048 A1 | 12/2006 | Lebo | |
| 2007/0033836 A1* | 2/2007 | Rasmussen | A43B 1/0081 36/50.1 |
| 2007/0107257 A1 | 5/2007 | Laska | |
| 2007/0169380 A1 | 7/2007 | Borsoi | |
| 2007/0191749 A1* | 8/2007 | Barberio | A43B 7/08 602/23 |
| 2007/0261269 A1* | 11/2007 | Petrie | A43C 11/008 36/50.1 |
| 2008/0052962 A1 | 3/2008 | Battilana | |
| 2008/0066344 A1* | 3/2008 | Kelley | A43C 11/1493 36/50.1 |
| 2008/0110059 A1 | 5/2008 | Kuramoto et al. | |
| 2008/0148602 A1 | 6/2008 | Marechal | |
| 2008/0168685 A1 | 7/2008 | Kim et al. | |
| 2008/0201987 A1 | 8/2008 | Bell | |
| 2008/0235995 A1* | 10/2008 | Reagan | A43B 3/0031 36/117.1 |
| 2008/0313926 A1 | 12/2008 | Kelley | |
| 2009/0071037 A1* | 3/2009 | Foxen | A43B 5/18 36/89 |
| 2009/0076428 A1* | 3/2009 | Kay | A61F 5/0111 602/27 |
| 2009/0090023 A1 | 4/2009 | Rackiewicz | |
| 2009/0094862 A1 | 4/2009 | Krauss | |
| 2009/0100649 A1* | 4/2009 | Bar | A43C 11/008 24/306 |
| 2009/0107012 A1 | 4/2009 | Cheney | |
| 2009/0112140 A1* | 4/2009 | Gaylord | A61F 5/0111 602/27 |
| 2009/0139113 A1 | 6/2009 | Buethorn | |
| 2009/0247920 A1* | 10/2009 | Clements | A61F 5/0127 602/27 |
| 2009/0300947 A1 | 12/2009 | Babolat | |
| 2010/0036304 A1* | 2/2010 | Norton | A43B 7/20 602/27 |
| 2010/0107452 A1 | 5/2010 | Baychar | |
| 2010/0126043 A1 | 5/2010 | Loverin | |
| 2010/0251564 A1* | 10/2010 | Meschter | A43B 23/0225 36/28 |
| 2010/0263236 A1 | 10/2010 | Carboy | |
| 2010/0304937 A1 | 12/2010 | Spencer | |
| 2011/0000103 A1 | 1/2011 | Hahn | |
| 2011/0010965 A1 | 1/2011 | Shepherd | |
| 2011/0030244 A1* | 2/2011 | Motawi | A43B 3/0031 36/117.1 |
| 2011/0113650 A1* | 5/2011 | Hurd | A43B 7/20 36/107 |
| 2013/0255105 A1* | 10/2013 | Bishop | A43B 3/126 36/88 |
| 2014/0114223 A1 | 4/2014 | Ingimundarson | |
| 2016/0270484 A1* | 9/2016 | Zadnik | A43B 23/0205 |
| 2016/0353833 A1* | 12/2016 | Hesterberg | A43B 13/223 |
| 2017/0265573 A1* | 9/2017 | Beers | A43C 11/14 |
| 2018/0242692 A1* | 8/2018 | Houng | A43C 11/1493 |
| 2018/0295942 A1* | 10/2018 | Drake | A43B 11/00 |
| 2019/0313742 A1* | 10/2019 | Bell | A43C 5/00 |

* cited by examiner

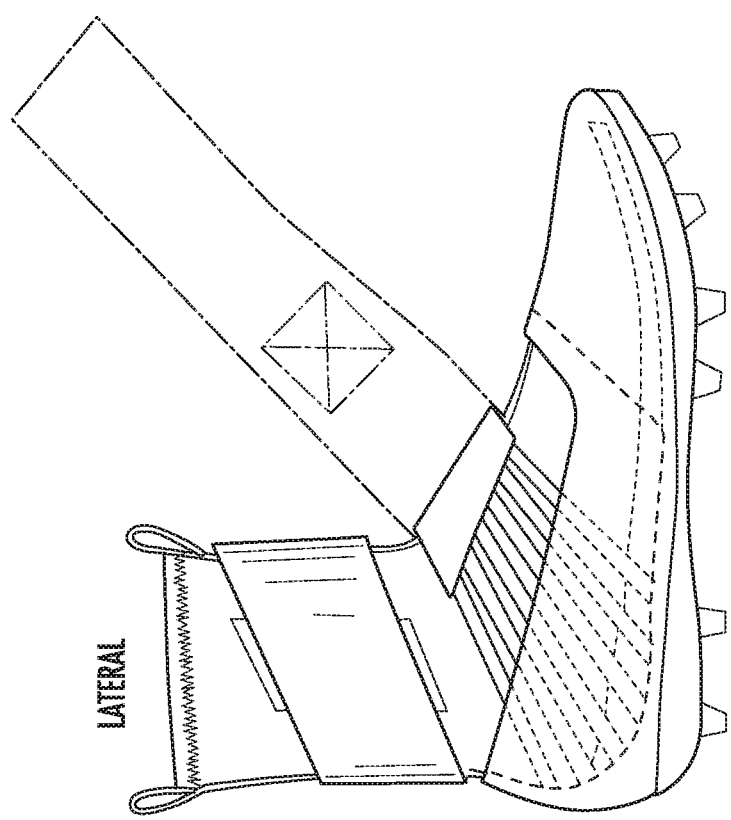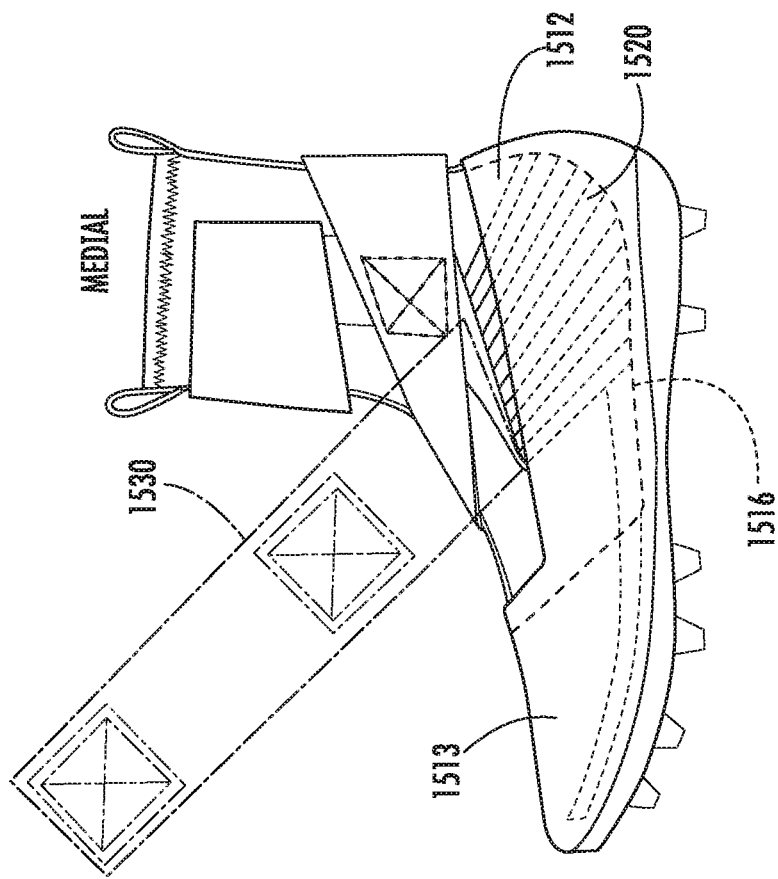
FIG. 15

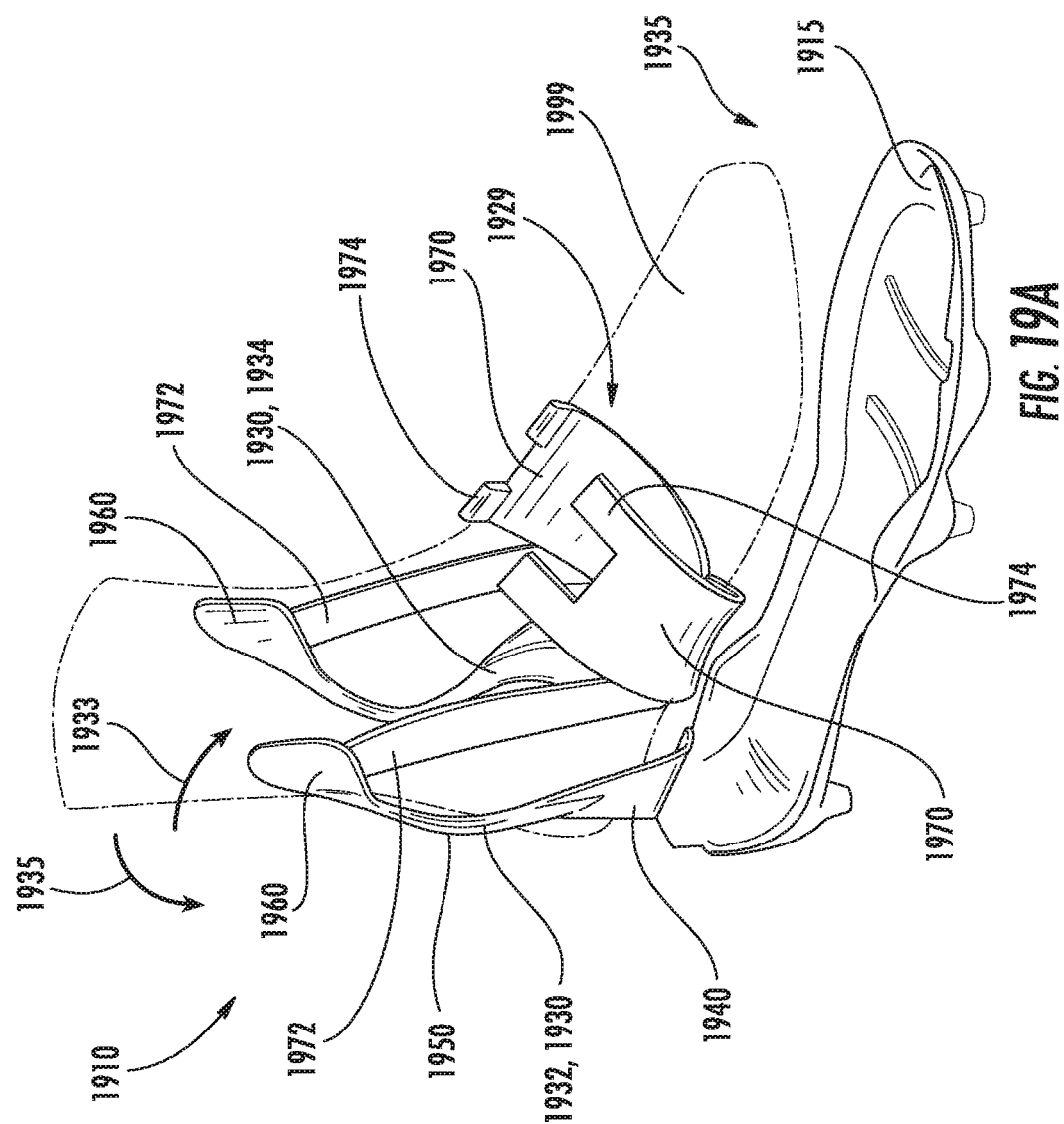

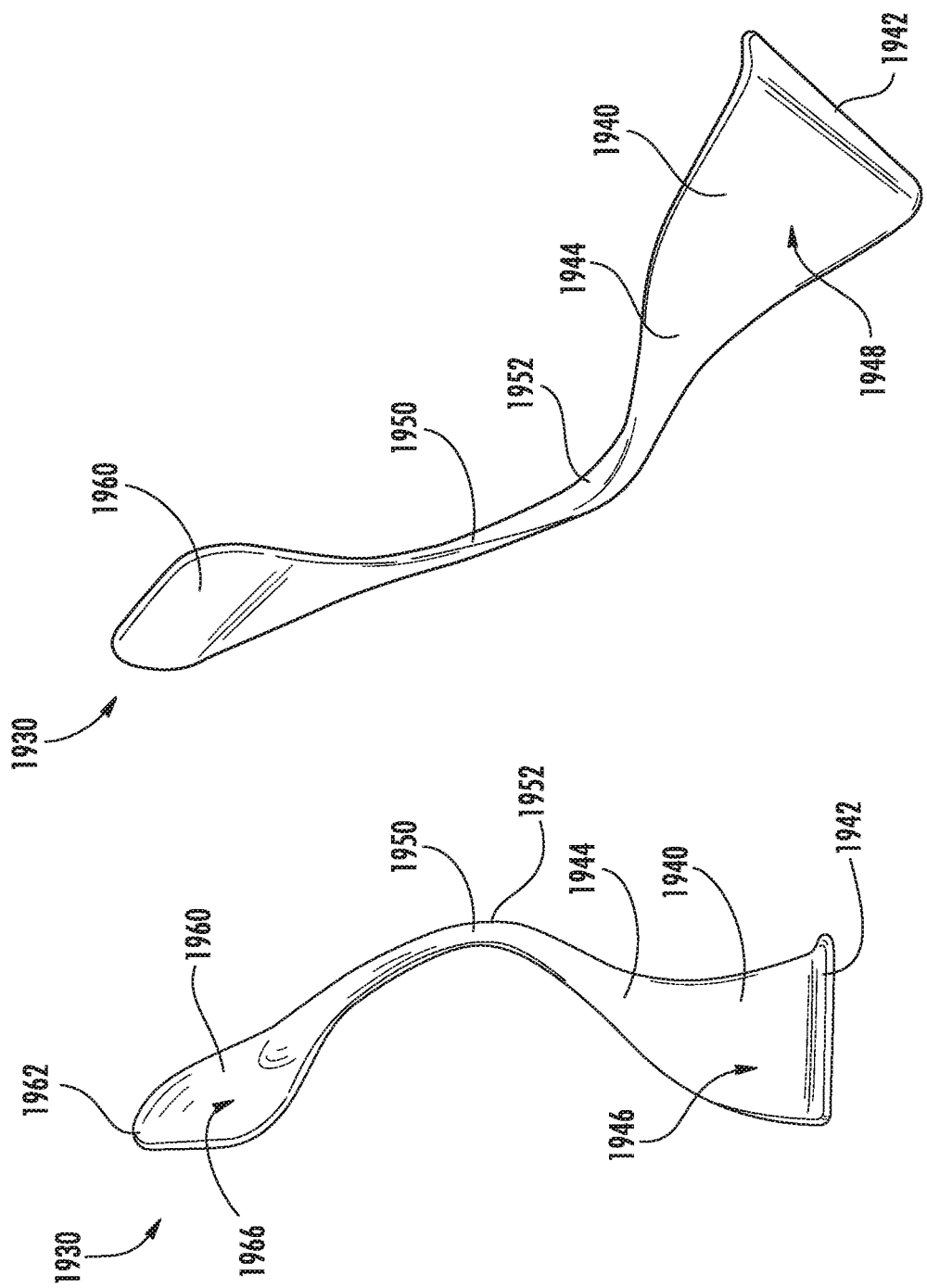

FOOT SUPPORT ARTICLE

CROSS REFERENCE TO RELATED APPLICATIONS

The present application is a continuation of U.S. application Ser. No. 14/013,684, filed 29 Aug. 2013 and entitled "Foot Support Article," which is a divisional of U.S. application Ser. No. 13/157,023, filed 9 Jun. 2011 and entitled "Foot Support Article," which is a continuation-in-part of U.S. application Ser. No. 13/111,704, filed 19 May 2011 and entitled "Foot Support Article," which claims priority to U.S. Provisional Application No. 61/357,075, filed on 21 Jun. 2010 and entitled "Foot Support Article." The disclosure of each of the aforementioned applications are incorporated herein by reference in its entirety.

FIELD

The present disclosure relates generally to articles of footwear, and, more particularly, to articles of footwear having foot support members.

BACKGROUND

Ankle stability is a key and critical need from athletes and users who deal with lateral motion. There exists a need to provide a simple and lightweight cleat or shoe for athletes in order to offer better support for the foot and ankle region of a user wearing the cleat. Athletes and users take a tremendous amount of time and effort to tape and spat their feet, as well as add additional ankle and foot support braces. The ankle support systems add weight to a footwear system in which lightness is highly desired.

Injuries to the ankle are estimated to account for 15-20% of all musculoskeletal injuries, with approximately 85% being ankle sprains. The most common mechanism of injury is excessive Inversion, coupled with Plantar Flexion—approximately 75-80% involve the lateral ligament complex, primarily the Anterior Talofibular Ligament.

Typically, ankle sprains occur in 40-100 ms. Compared to average muscle latencies: reported latency of 69-85 ms, with approximately 90-110 ms to reach half max force, and an average of 250 ms to reach peak torque generation, the body is not able to adequately respond to an unexpected inversion. In comparison, during running, the stance phase lasts 200-250 ms, and the calf muscles are activated approximately 150 ms prior to heel impact, allowing the ankle adequate time to stabilize.

Players with a history of ankle sprains are 2-3 times more likely to have a recurrent injury than players without history of ankle injuries. Use of bracing or taping, as well as proprioceptive training have been shown to reduce the level of recurrence to the levels of players without history of injury.

In general, both bracing (lace-up and semi-rigid) and taping have been shown to reduce both the frequency and severity of ankle sprains during athletic activities. Semi-rigid braces tend to have a more positive effect for individuals with a history of ankle sprains than for athletes without history. Such lacing and taping methods currently used are time consuming and a waste of resources. Upon the completion of use, the user cuts off and discards the taping. This process increases the time and cost of providing support for the foot and ankle during athletic activities. Thus, improvements to support members that brace the foot and ankle of a person wearing the bracing are beneficial.

SUMMARY

In at least one embodiment, an article of footwear includes a sole, an upper defining a foot cavity, and a brace member. The brace member is comprised of a non-elastic resilient material. The brace member is positioned within a pocket in the upper and extends from a heel portion to above an ankle portion of the upper.

In at least one embodiment, the brace member includes a top plate member and a base plate member with a central shaft extending between the top plate member and the base plate member. The central shaft portion may be a C-shaped shaft that extends around a rear portion of an ankle of a wearer (i.e., a dorsal side of the ankle). The C-shaped shaft portion includes an inflection point that is wider than other portions of the C-shaped shaft.

In at least one embodiment, an article of footwear comprises a sole and a shoe upper connected to the sole. The shoe upper and the sole define a foot cavity configured to receive a human foot. Laces are positioned on the upper and configured to tighten the shoe upper on the human foot. An elastic wrap member is positioned in the foot cavity. The elastic wrap member is configured to stretch and when the laces tighten the upper on the human foot. In at least one embodiment, the elastic wrap member includes a cradle portion that extends from a heel portion to a top portion of the upper within the foot cavity and is configured to only partially surround the human foot within the foot cavity.

The above described features and advantages, as well as others, will become more readily apparent to those of ordinary skill in the art by reference to the following detailed description and accompanying drawings. While it would be desirable to provide an apparatus that provides one or more of these or other advantageous features as may be apparent to those reviewing this disclosure, the teachings disclosed herein extend to those embodiments which fall within the scope of any appended claims, regardless of whether they include or accomplish one or more of the advantages or features mentioned herein.

BRIEF DESCRIPTION OF THE DRAWINGS

FIG. 15 is an illustration depicting tensioning members attached to a strap in an article of footwear.

FIG. 19A is an illustration of an alternative embodiment of an article of footwear including support braces carried by the shoe upper.

FIG. 19E shows a view of an inner face of the support brace of FIG. 19A.

FIG. 19F shows a perspective view of the support brace of FIG. 19A.

DETAILED DESCRIPTION

Figure 1A:
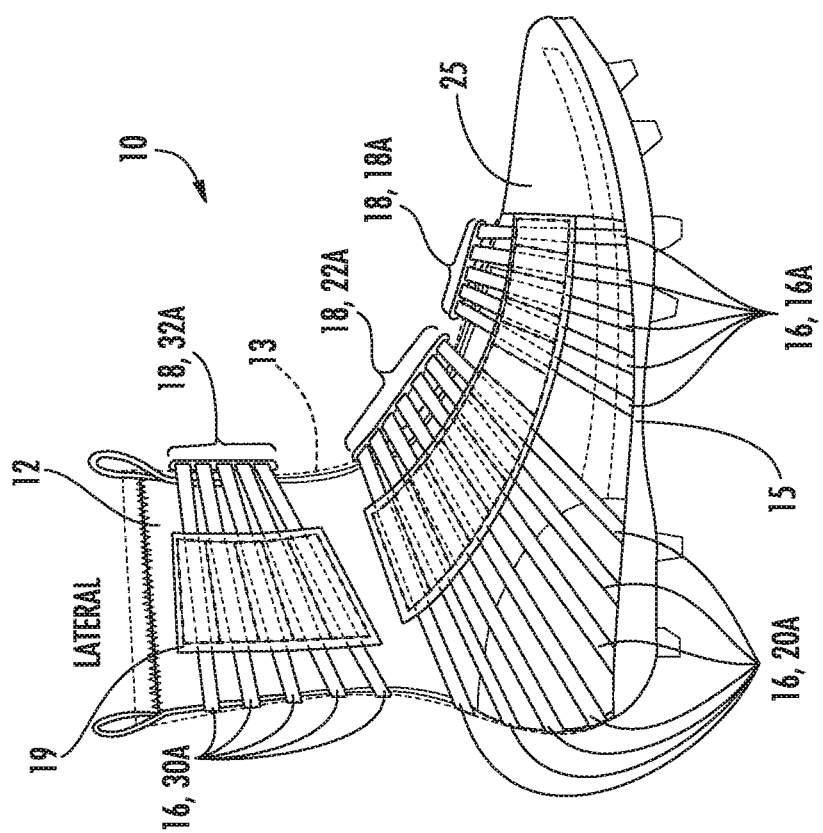
FIG. 1A is a cutaway medial side view illustrating the placement of tension members in an article of footwear.

For a general understanding of the details for the footwear disclosed herein, the drawings are referenced throughout this document. In the drawings, like reference numerals designate like elements. As used herein the term "foot" may refer to a portion of the human foot, a full human foot, and to the ankle. Various portions of the foot include, but are not limited to, the forefoot, midfoot, upper foot, heel, and ankle. The terms "medial" and "medial side" refer to the inner side of a foot extending from the large toe to the heel, and the terms "lateral" and "lateral side" refer to the outer side of the foot extending from the small toe to the heel. The term "user" may refer to a person wearing an article of footwear or another person such as an athletic trainer. The user may adjust the article of footwear to apply compression and support to the foot as described herein.

Article of Footwear with Tensioning Members

Figure 1B:
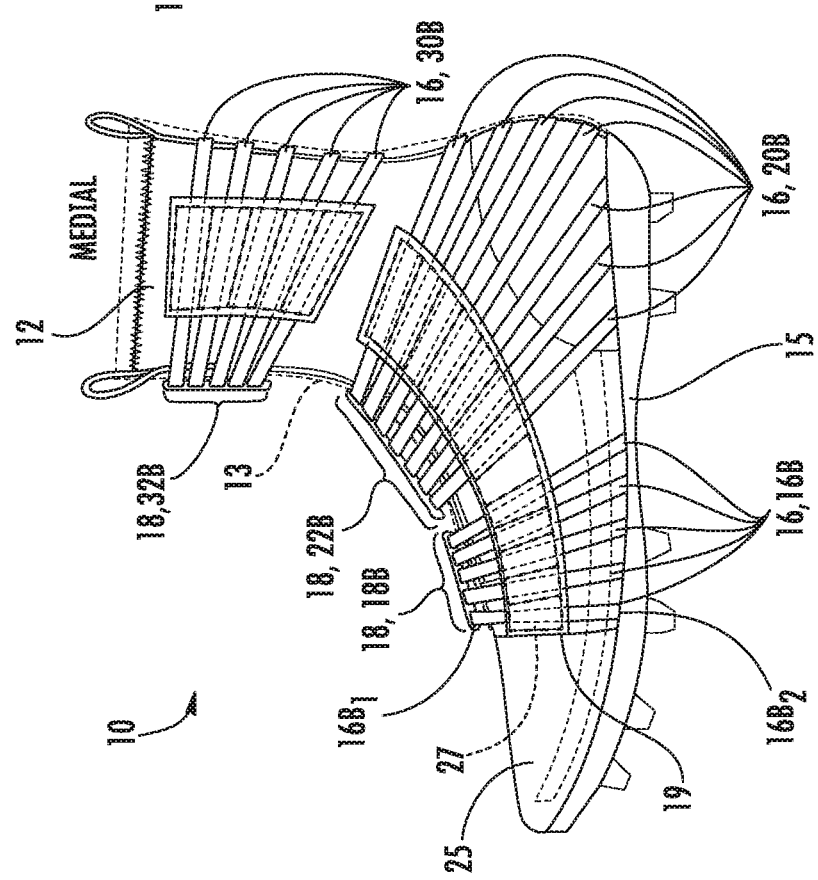
FIG. 1B is a cutaway lateral side view illustrating the placement of tension members in the article of footwear depicted in FIG. 1A.

FIGS. 1A-8 depict an article of footwear, embodied here as a cleat 10, having an inner layer 12 positioned inside of an outer shell 13 (illustrated by dotted line 13 in FIG. 1A and FIG. 1B). FIG. 1A depicts the medial side of cleat 10, while FIG. 1B depicts the lateral side of the cleat 10. FIG. 2A and FIG. 2B depict the cleat 10 including features omitted from FIG. 1A and FIG. 1B for clarity. Cleat 10 includes an inner layer 12 that conforms to the foot and ankle region of a user. The cleat 10 includes tensioning members 16 that may be adjusted by the user of the cleat 10 to provide compression to various portions of the foot 14 after the foot 14 is inserted into the cleat 10. Tensioning members 16 include three sets of tensioning members, including forefoot tensioning members 16A 16B, midfoot tensioning members 20A 20B, upper foot tensioning members 30A-30B, and tensioning straps 52, as explained below. The forefoot tensioning members 16A-16B include a first plurality of tensioning members 16 that are elongated and arranged side-by-side such that they are generally aligned in a forefoot region of the cleat 10. The midfoot tensioning members 20A-20B include a second plurality of tensioning members 16 that are elongated and arranged side-by-side such that they are generally aligned in a midfoot region of the cleat 10. The upper foot tensioning members 30A-30B include a third plurality of tensioning members 16 that are elongated and arranged side-by-side such that they are generally aligned in an upper foot region of the cleat 10. Cleat 10 may be worn on a foot 14 that is inserted inside of the cleat 10. While the illustrations of FIG. 1A-FIG. 1B depict different numbers of tensioning members than FIG. 2A-FIG. 2B, it will be understood that these figures depict the same embodiment of an article of footwear and that the different numbers of tensioning members 16 seen in FIG. 1A-FIG. 1B are simply intended to illustrate that different numbers and arrangements of tensioning members 16 are possible within various embodiments of the article of footwear. While FIG. 1A-FIG. 2B depict a cleat 10 with one or more spikes 17 or other projections, alternative embodiments may include any suitable shoe, footwear, boot, and other articles that may be worn around the ankle and/or foot.

The inner layer 12 may be comprised of any material that provides the user with comfort and functionality. Such materials include, but are not limited to, compression fabrics, polypropylenes, webbing, neoprene, elastane, synthetics, and the like. The inner layer 12 may be formed as a flexible boot or sock that conforms to the foot and ankle. The inner layer 12 accommodates the foot 14 and is configured to fit snugly about the foot and ankle 14. As seen in FIG. 1A and FIG. 1B, one or more sleeves 19 may be affixed to the inner layer 12. The sleeve 19 separates the tensioning members 16 from the outer shell 13 and includes one or more channels 27. Channels 27 enclose the tensioning members 16 to enable tightening and loosening of the tensioning members 16 and to prevent tangling of the different tensioning members 16 in the article of footwear 10. Similar to the tensioning members 16, the channels 27 are also arranged side-by-side such that they are generally aligned in each associated region of the cleat, as shown in FIG. 1A and FIG. 1B. In the embodiment of FIG. 1A and FIG. 1B, the article of footwear 10 provides a channel for each tensioning member in the article of footwear, but alternative configurations may include channels 27 for only a limited number of the tensioning members 16.

The outer shell 13 may be formed from one or more flexible materials that enclose some or all of the inner layer 12. Such materials include, but are not limited to, natural and synthetic leather, fabrics including nylon and canvas, rubber, and plastics. The outer shell 13 includes a lower portion or sole 15 that is attached to an upper portion 25, referred to as an "upper" that is attached to the sole 15. The sole 15 and upper 25 form a volume that is referred as a "foot cavity". The foot cavity accommodates the foot of a person wearing the cleat 10. The foot cavity also holds the inner layer 12 and portions of the tensioning members 16. In various alternative embodiments described below, different support members and stabilizing members are also positioned inside the foot cavity. The inner layer 12 may be permanently attached to the outer shell 13 of the cleat 10, or alternatives the outer shell 13 may be selectively removable from the inner layer 12 to aid in fitting the cleat 10 to the foot.

As shown in FIG. 1A-FIG. 8, the plurality of tensioning members 16, include forefoot tensioning members 16A and 16B, midfoot tensioning members 20A and 20B, upper foot tensioning members 30A and 30B, and tensioning straps 50A and 50B. Each of the tensioning members 16 may be adjusted to apply a selected compressive force to a corresponding region of the foot 14 inside of the cleat 10. As exemplified by forefoot tensioning member 16B in FIG. 1A, each of the tensioning members 16 in cleat 10 has a first end 16B1 attached to the inner layer 12 inside of the foot cavity, and a second end 16B2 that extends to a position outside of the foot cavity and the outer shell 13, depicted with a dotted line in FIG. 1A-FIG. 1B. In the example embodiment of cleat 10, the end 16B2 that extends outside of the outer shell 13 is attached to a tab 18B. Tab 18B is one of the tension adjustment members 18 shown with cleat 10. The tension adjustment members 18 provide a surface that the user may grip to tighten or loosen the tensioning members 16 that are attached to the corresponding tab 18. The tension adjustment members 18 are also configured to be secured to the outer shell 13 or otherwise locked in place in order to enable the tensioning members 16 to continue to apply a compressive force to the foot 14 after the user adjusts and releases the tensioning members 16. The tensioning members 16 included in cleat 10 are described in more detail below.

Figure 2A:
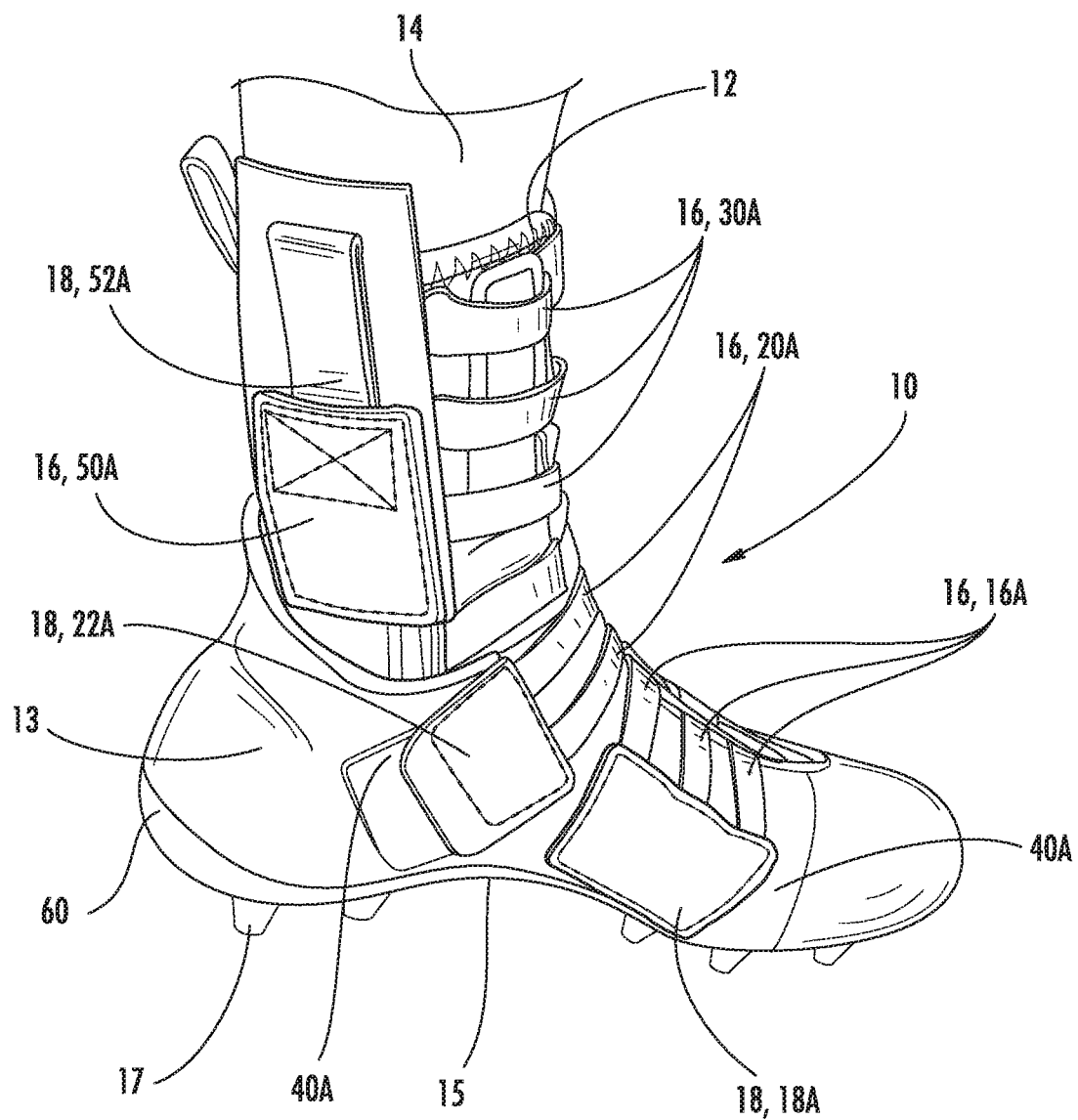
FIG. 2A is a side view illustrating the medial side of the article of footwear depicted in FIG. 1A.
Figure 2B:
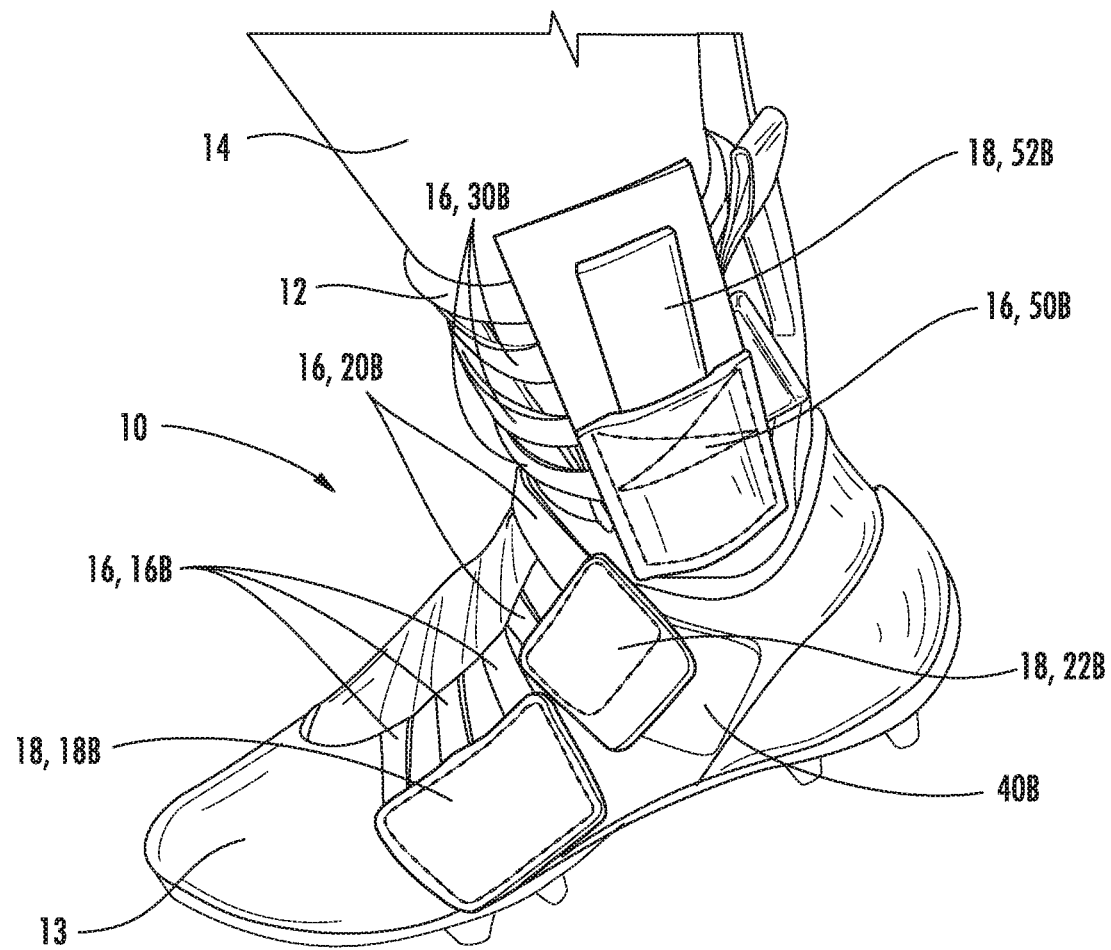
FIG. 2B is a side view illustrating the lateral side of the article of footwear depicted in FIG. 1B.
Figure 3:
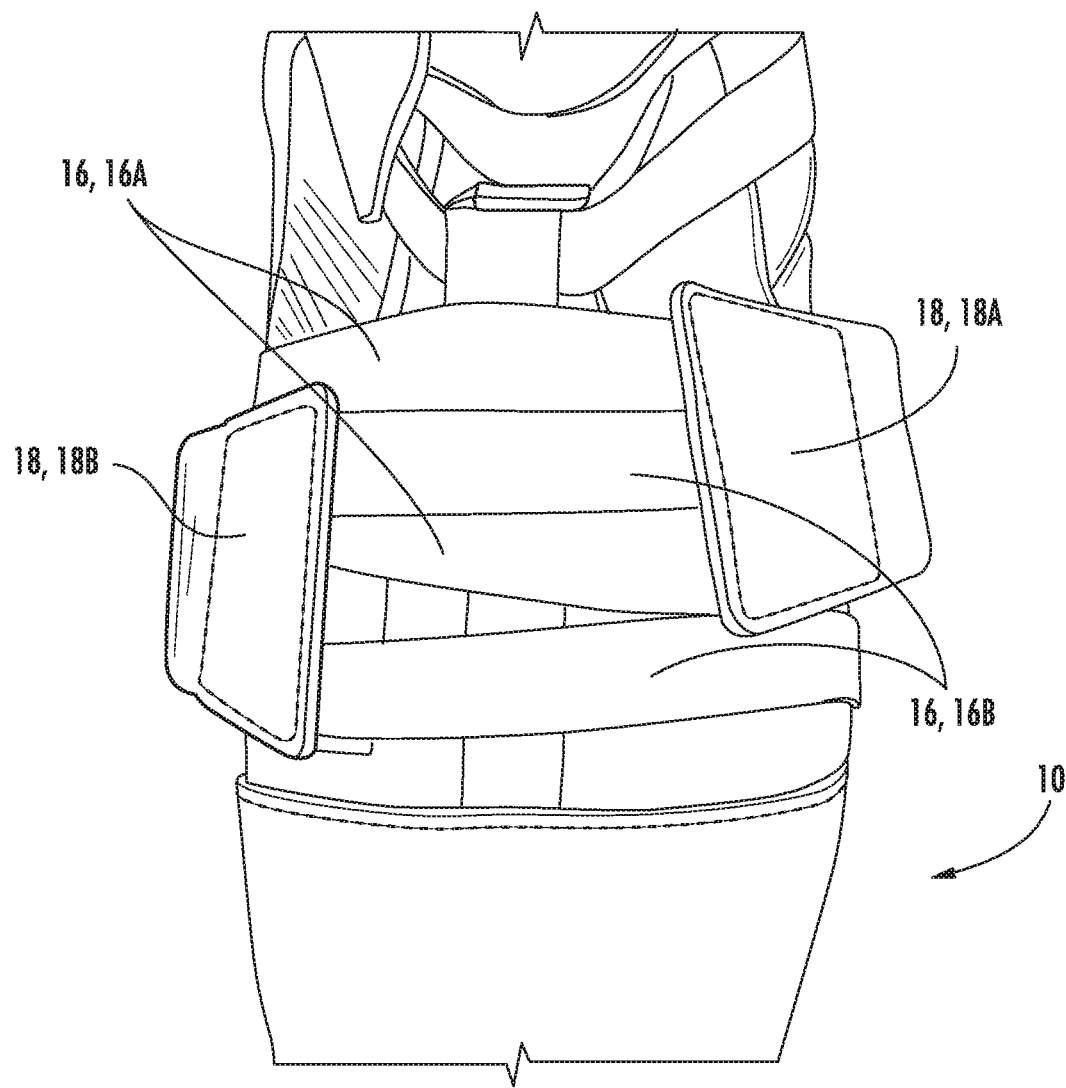
FIG. 3 is a top view of tensioning members positioned above the forefoot in the article of footwear depicted in FIG. 2A and FIG. 2B.
Figure 4:
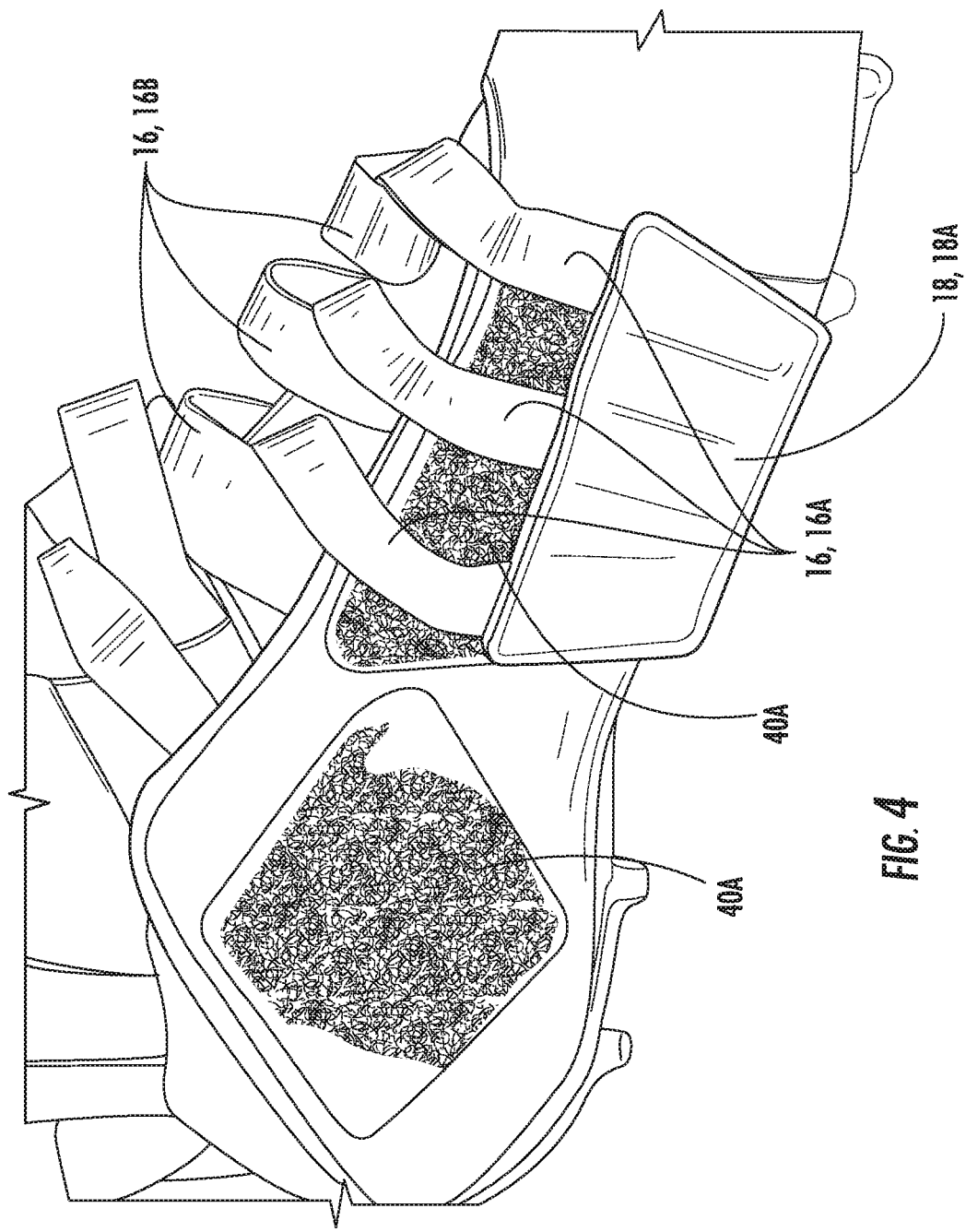
FIG. 4 is a side view of adjustment members in the article of footwear depicted in FIG. 2A and FIG. 2B.

The exemplary embodiment of cleat 10 includes two sets of crisscrossing forefoot tensioning members 16A and 16B. As illustrated in FIGS. 1A-2B as well as FIGS. 3, and 4, forefoot tensioning members 16A-16B are located on a forefoot region of the cleat 10. FIG. 1B depicts one set of forefoot tensioning members 16A that are attached to the lateral side of the inner layer 12 and cross to the medial side of the cleat 10. FIG. 1A depicts another set of the forefoot tensioning members 16B that are attached to the medial side of the inner layer 12 and cross to the lateral side of the cleat 10. The tensioning members 16A and 16B are shown as straps formed from an inelastic fabric material. Alternative tensioning member configurations may use one or more members formed from an elastic or inelastic material, including one or more elastic bands that are configured to stretch in response to tension. FIG. 2A-FIG. 3 depict the tensioning members 16A and 16B arranged in a crisscross pattern. The ends of each set of tensioning members 16A and 16B positioned outside of the outer shell 13 are affixed to one of a pair of forefoot tabs 18A and 18B, respectively. The forefoot tabs 18A and 18B each engage with one of corresponding fastening pads 40A and 40B, respectively, positioned on the outer shell 13 of the cleat 10.

As best shown in FIGS. 1A-1B, 2A-2B, and 4, tabs 18A and 18B include a hoop or loop material on an inner side designed to engage an opposing hook and loop material on the fastening pads 40A and 40B. The hooks may be either unidirectional or multidirectional. Fastening pads 40A and 40B are examples of fastening locations, which are predetermined locations positioned on the outer shell 13 that are configured to fasten one or more tensioning members in place. In lieu of to the hook and loop material, any fastener that holds the tabs 18 in position with respect to the outer shell 13 may be used including, for example, nanoadhesive materials, and snap closures. The tensioning members 16 may include ridged structures that engage a ratcheting fastening location to enable the tensioning member to lock in place. A lever or dial 21 may provide mechanical advantage to enable application of force to tighten and loosen tensioning member.

Figure 5:
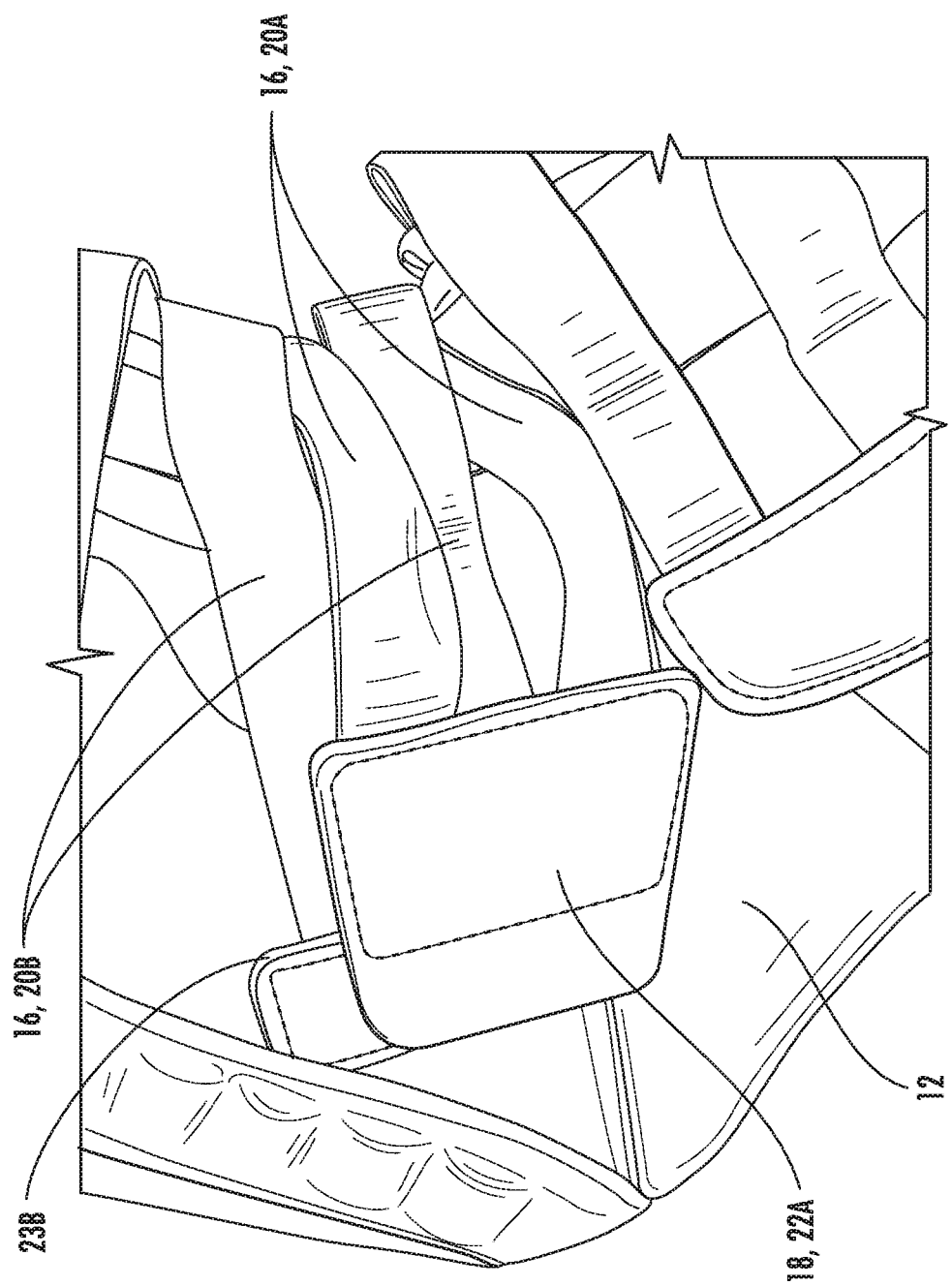
FIG. 5 is a view of the tensioning members that are configured to engage a midfoot portion of a foot in the article footwear depicted in FIG. 2A and FIG. 2B.

As illustrated in FIG. 1A-FIG. 2B, in conjunction with FIG. 5, midfoot tensioning members 20A and 20B are located in a midfoot region of the cleat 10. The midfoot tensioning members 20A are attached to the lateral side of the inner layer 12 and extend to the medial side of the outer shell 13 terminating in midfoot tab 22A. The midfoot tensioning members 20B are attached to the medial side of the inner layer 12 and extend to the lateral side of the outer shell 13 terminating in midfoot tab 22B. FIG. 5 depicts midfoot tensioning members 20B stitched to member 23B that attaches the tensioning members 20B to the inner layer 12. The midfoot tensioning members 22A and 22B are arranged in a crisscross pattern across the midfoot region. Midfoot tabs 22A-22B are configured to engage with a corresponding attachment pad 40A-40B positioned on the outer shell 13 in a similar manner to the forefoot tensioning members 16A-16B.

Figure 6:
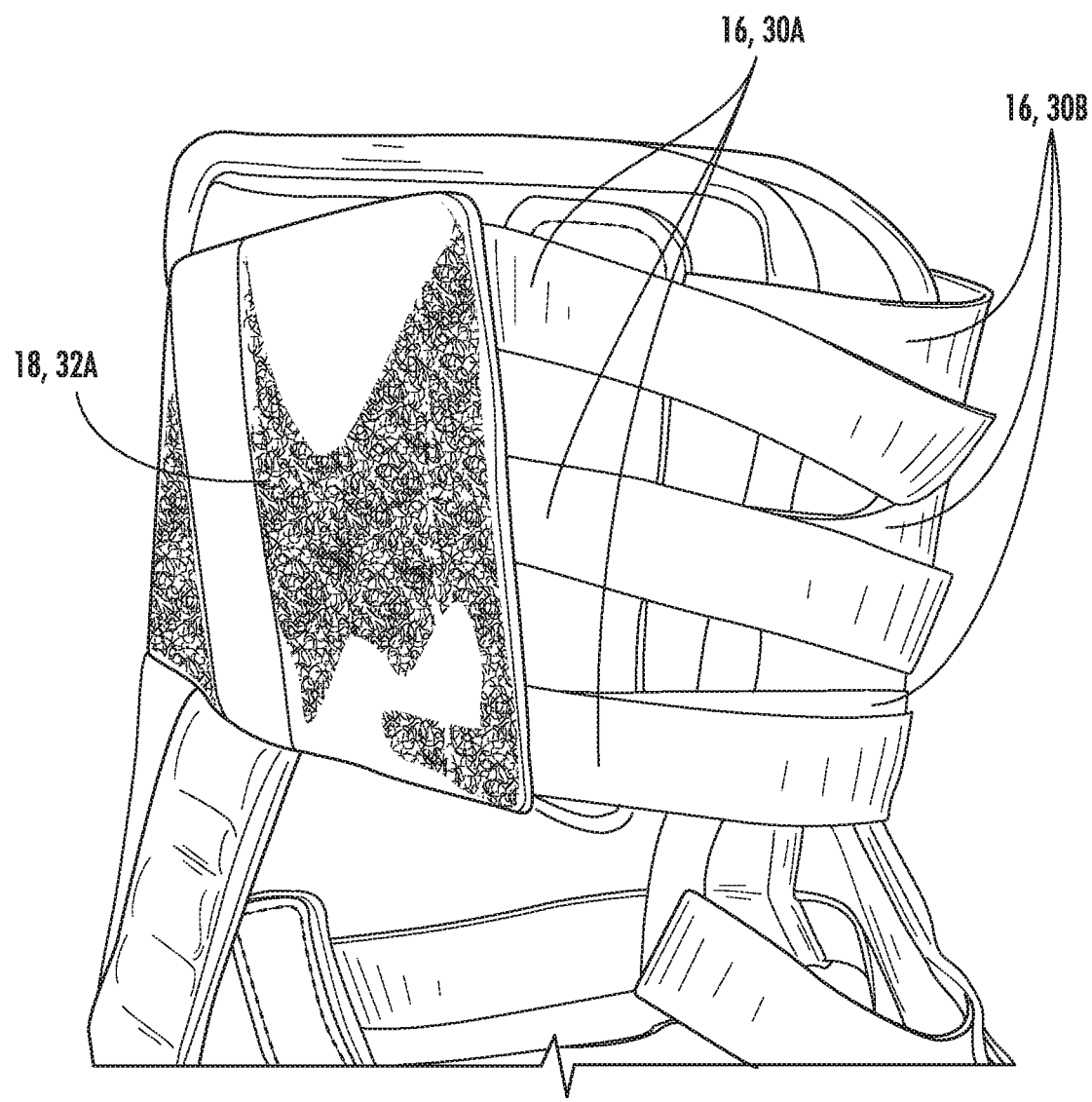
FIG. 6 is a view of tensioning members that are configured to engage an ankle in the article of footwear depicted in FIG. 2A and FIG. 2B.
Figure 8:
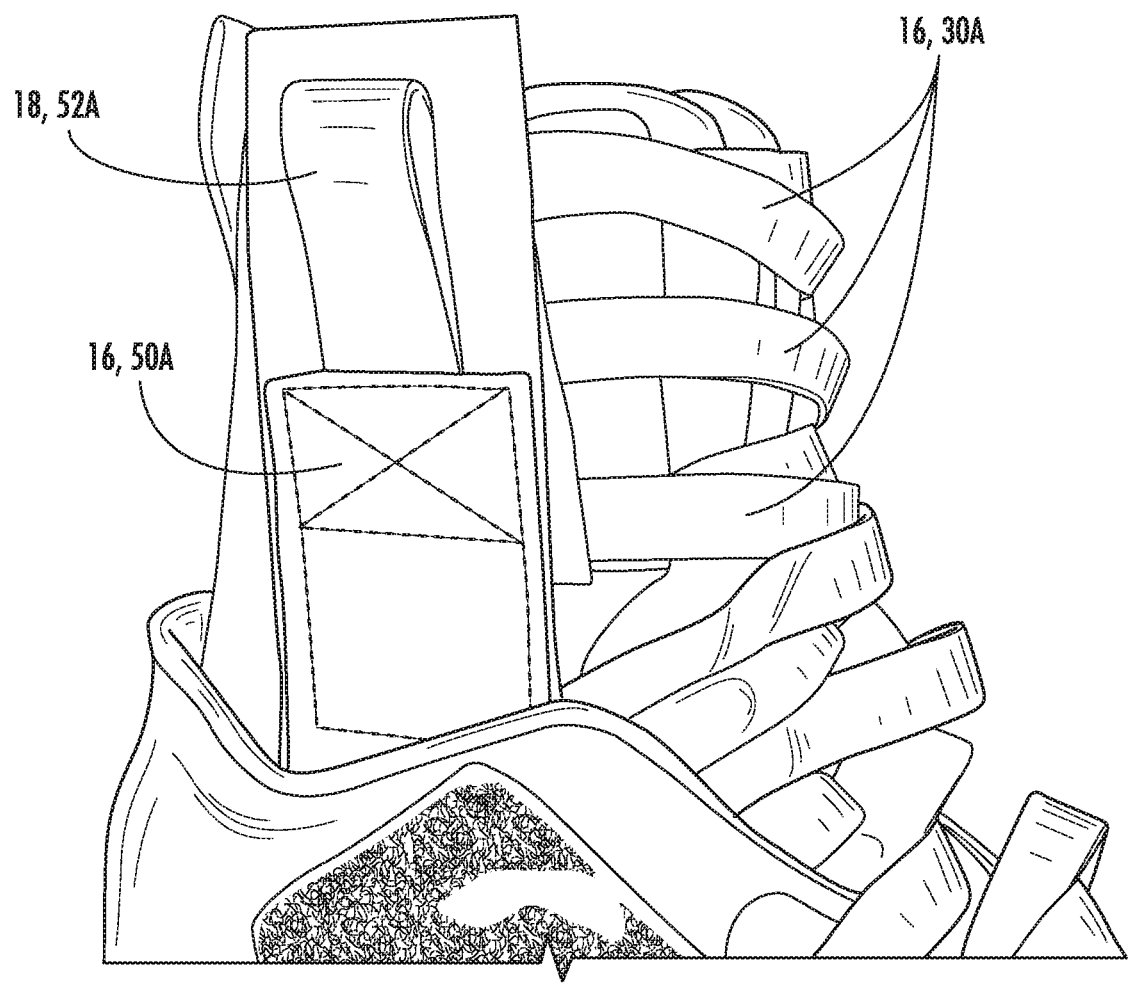
FIG. 8 is a view of a tensioning strap and support members positioned around an upper portion of a foot and ankle in the article of footwear depicted in FIG. 2A and FIG. 2B.

As illustrated in FIG. 1A-FIG. 2B in conjunction with FIG. 6 and FIG. 8, upper foot tensioning members 30A and 30B are located in an ankle and upper foot region of the cleat 10. The upper foot tensioning members 30A are attached to the lateral side of the inner layer 12 and cross to the medial side, terminating in an upper foot tab 32A. Upper foot tensioning members 30B are attached to the medial side of the inner layer 12 and extend to the lateral side, terminating in a second upper foot tab 32B. The upper foot tensioning members 30A and 30B are arranged in a crisscross pattern across the upper foot region. Upper foot tabs 32A and 32B have a hook and loop material on an inner side and outer side of each tab. The hook and loop material on the inner side fastens to a corresponding hook and loop fastener positioned on the outer shell 13. The hook and loop material on the outer side of each of the upper foot tabs 32 provides a fastening location for one of the tensioning straps 50A and 50B. As explained in further detail below, a user may adjust the tension of the upper foot tensioning members 30A and 30B and then secure the tabs 32A and 32B to the outer shell 13 in order to apply a continuing compressive force to the foot.

Figure 7:
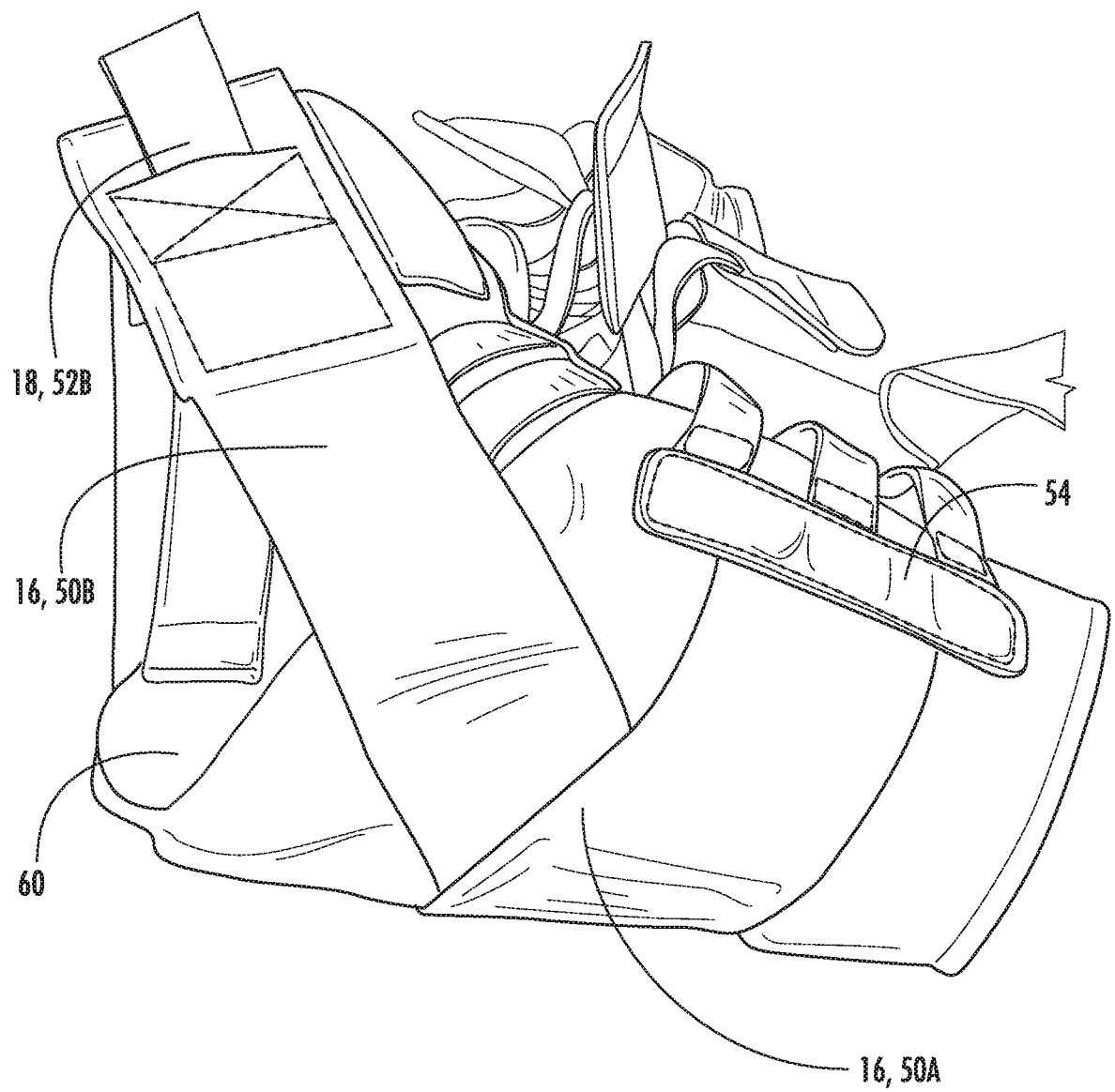
FIG. 7 is a view of an inner layer surrounding a sole of a foot in the article of footwear depicted in FIG. 2A and FIG. 2B.

With particular reference to FIG. 2A-FIG. 2B in conjunction with FIG. 7 and FIG. 8, the cleat 10 further includes a pair of tensioning straps 50A and 50B. Each of the tensioning straps 50A and 50B has one end attached to the inner layer 12, and a second end attached to a pull tab 52. As shown in FIG. 7, tensioning strap 50A has one end 54 attached to the inner layer 12, and the tensioning strap 50A is routed underneath the foot. A second tensioning strap 50B crosses the first tensioning strap 50A, extends longitudinally from the heel 60, and terminates at a pull tab 52. FIG. 1, FIG. 2, and FIG. 7 show cleat 10 with two tensioning straps 50A and 50B. An alternative embodiment, however, may only use a single tensioning strap. The tensioning straps 50A and 50B crisscross and run substantially longitudinally along the ankle and lower leg and terminating with pull tabs 52A and 52B, respectively. Pull tabs 52A and 52B include a hook and loop fastener material that compliments the material on the outer surface of the upper foot tabs 32. While in the present embodiment, tensioning straps 50A and 50B are shown as attached in the vicinity of the midfoot and forefoot, an alternate embodiment includes adjustable attachment means, such as hook and loop fasteners, rather than permanent attachment.

In operation, the user first inserts a foot 14 inside the inner layer 12 positioned in the foot cavity formed inside the sole 15 and upper 25. The foot 14 slides into the inner layer 12 and seats the heel of the foot into the heel portion 60. When inserting the foot 14, tabs 18A-18B, 22A-22B, 32A-32B and the pull tabs 52A-52B are disengaged from counterpart fastening locations. The user may then apply a compressive force to the foot 14 using one or more of the tensioning members 16 on the cleat 10. In one embodiment, the user pulls forefoot tabs 18A and 18B away from each other to apply a tensile force that tightens the forefoot tensioning members 16A and 16B. The user engages the forefoot tab 18A-18B with the forefoot of the cleat 10 thus maintaining and locking in the applied tension on the forefoot tensioning members 16A-16B. The user pulls midfoot tabs 22A and 22B away from each other to applying a tensile force that tightens the midfoot tensioning members 20A and 20B. The user then engages the midfoot tabs 22A and 22B with the midfoot of the cleat 10 thus maintaining and locking in the applied tension on the midfoot tensioning members 20A and 20B. The user pulls upper foot tabs 32A and 32B away from each other to apply a tensile force that tightens the upper foot tensioning members 30A and 30B. The user then engages the upper foot tabs 32A and 32B with the upper foot of the cleat 10 thus maintaining and locking in the applied tension on the upper foot tensioning members 30A and 30B. The forefoot tensioning members 16A-16B, midfoot tensioning members 20A-20B, and the upper foot tensioning members 30A-30B may be tightened in any order.

Once tension has been applied to the tensioning members 16A-16B, 20A-20B, and 30A-30B, the user uses pull tabs 52 to pull and apply a tensile force to the tensioning straps 50. The user pulls the pull tabs 52 to apply a selected tensile force to the tensioning straps 50A and 50B, and engages pull tabs 52A and 52B with the upper foot tabs 32A and 32B, respectively, to secure the tensioning straps 50A and 50B in the selected position. The result of the aforementioned tensioning enables the user to fully lock the cleat 10 about the foot and ankle region. In an alternative embodiment, the tensioning straps 50A and 50B may have fastening material such as hook and loop material positioned on both sides of the tensioning straps 50A and 50B. In this embodiment, the user pulls on tensioning straps 50A and 50B to apply compression to the foot 14 prior to adjusting the upper foot tabs 32A and 32B.

When one of the tensioning members 16A-16B, 20A-20B, 30A-30B, and 50A-50B inside of the outer shell 13 is tightened, the effective length of the tightened tensioning member inside of the outer shell 13 decreases, and the effective length of the portion of the tensioning member that extends through the outer shell 13 increases. The term "effective length" refers to the proportion of the length of one or more of the tensioning members 16 that is either inside of or outside of the outer shell 13. As the effective length of one of the tensioning members 16 increases inside the outer shell 13, the corresponding effective length decreases outside of the outer shell 13, and vice versa. Each of the tensioning members 16A-16B, 20A-20B, 30A-30B, and 50A-50B may be loosened as well as tightened. Each tensioning member may be loosened when a corresponding tension adjustment member 18 for a tensioning member 16 is detached from a corresponding attachment location of the cleat 10. The user may loosen the tensioning member and then engage the tab with a corresponding attachment location to maintain the applied tension. When one of the tensioning members 16A-16B, 20A-20B, 30A-30B, and 50A-50B is loosened, the effective length of the loosened tensioning member inside of the outer shell 13 increases, and the effective length of the portion of the tensioning member that extends through the outer shell 13 decreases.

Article of Footwear with Support Members

Figure 9:
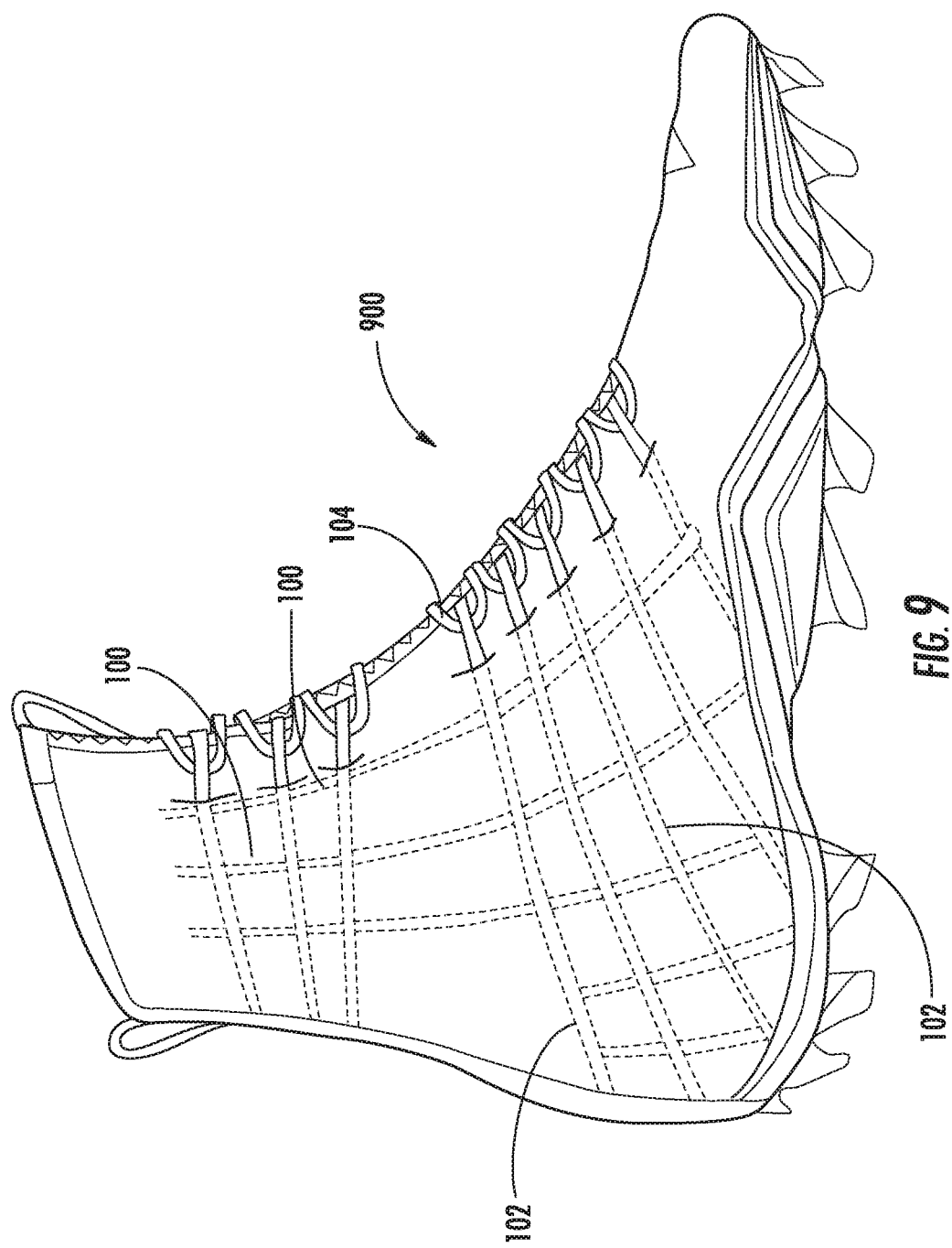
FIG. 9 is a side view of an alternative embodiment of footwear that includes support members incorporated into the footwear.
Figure 10:
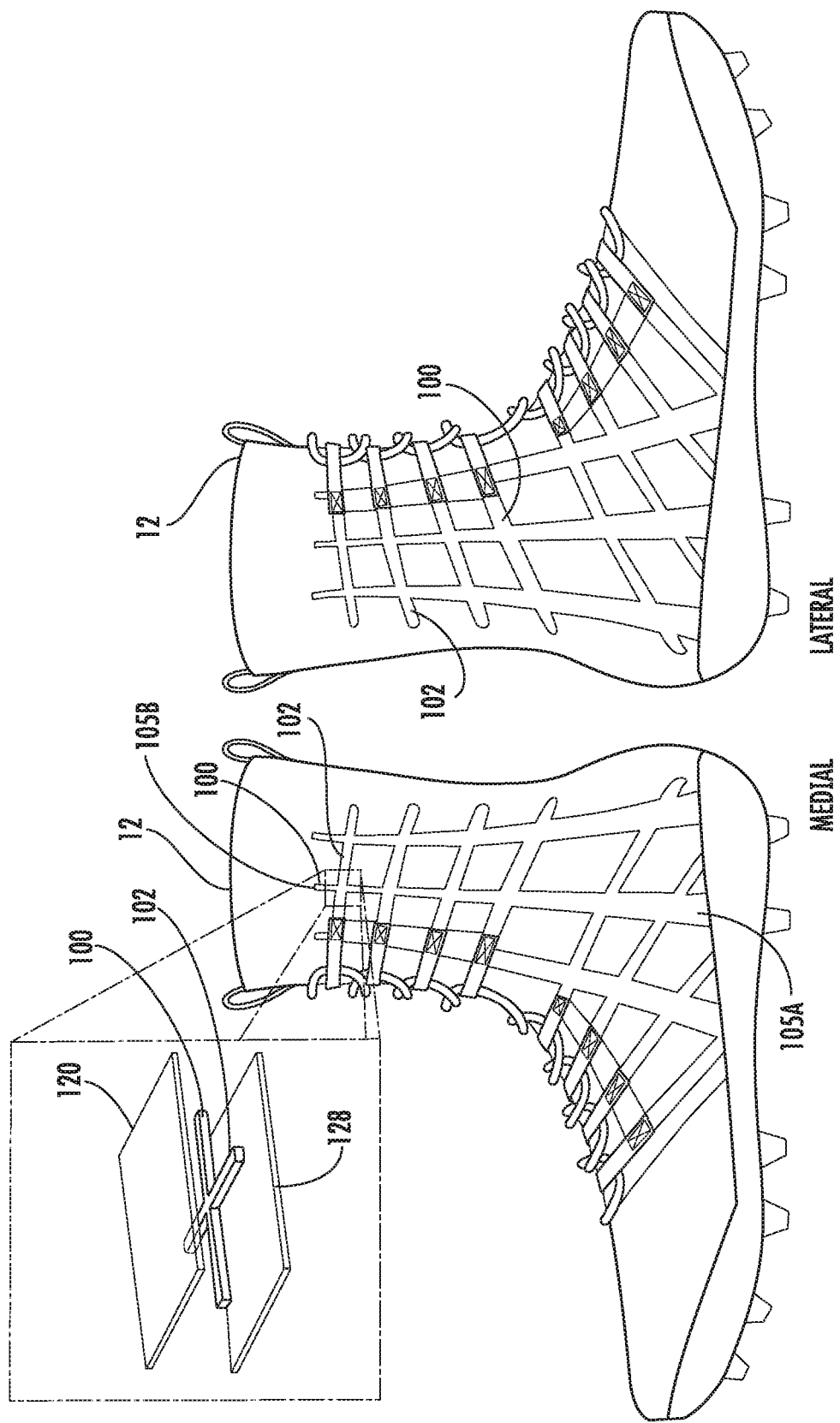
FIG. 10 is a cutaway side view illustrating horizontal and vertical supports on the medial and lateral sides of the article of footwear depicted in FIG. 9.

With reference to FIG. 9-FIG. 10, an alternative embodiment of an article of footwear 900 is disclosed that includes support members 100 and 102. The support members 100 and 102 enable the footwear article 900 to retain a predetermined shape and continue providing support to a foot inserted in the footwear article 900 when the various tensioning members described above apply compression to the foot 14. The support members 100 and 102 provide a stiffening force to the footwear article 900 to prevent the ankle and foot from rolling or spraining. The support members 100 and 102 may be incorporated with any of the embodiments of footwear and modifications thereof that are described in this application.

Footwear article 900 includes vertical supports 100 and horizontal supports 102 shown in FIG. 9. Vertical supports 100 are oriented in a substantially longitudinal direction with the ankle and lower leg of a foot inserted in the footwear article 900. The vertical supports 100 are integrated into an inner layer of the footwear article 900 similar to inner layer 12 seen above. Vertical supports 100 originate proximate the bottom of the inner layer and run the length thereof. The vertical supports 100 may be removable or permanently affixed to the inner layer. Additionally, the vertical supports may follow the contours of the foot. Additionally, the footwear article 900 may include horizontal supports 102 that are oriented in a substantially longitudinal with the foot inserted in the footwear article 900. The horizontal supports 102 may be operably connected to the eyelets or lacing system 104 of the footwear article 900 or to the tensioning members 16 described above.

As shown in FIG. 10, the vertical supports 100 and horizontal supports 102 may be formed from one or more members formed from a polymer such as a thermoplastic polyurethane (TPU) material. In the embodiment of FIG. 9 and FIG. 10, the TPU forming the supports 100 and 102 is approximately 3 mm thick, although different support configurations may have different thicknesses. Vertical supports 100 have a lower end 105A near the sole of the footwear 900 with a wider width that tapers to a narrower width at an upper end 105B proximate to the top of the footwear 900. The inner layer 12 may further comprise a top layer 120 formed from a stretchable fabric material and a bottom layer 128 formed by an elastic material. The bottom layer 128 faces the foot, while the top 120 engages the tensioning members 16 and outer shell. The vertical support members 100 and horizontal support members 102 are positioned between the top layer 120 and bottom layer 128.

Article of Footwear with Tensioning Member Channels Over Support Members

Figure 11:
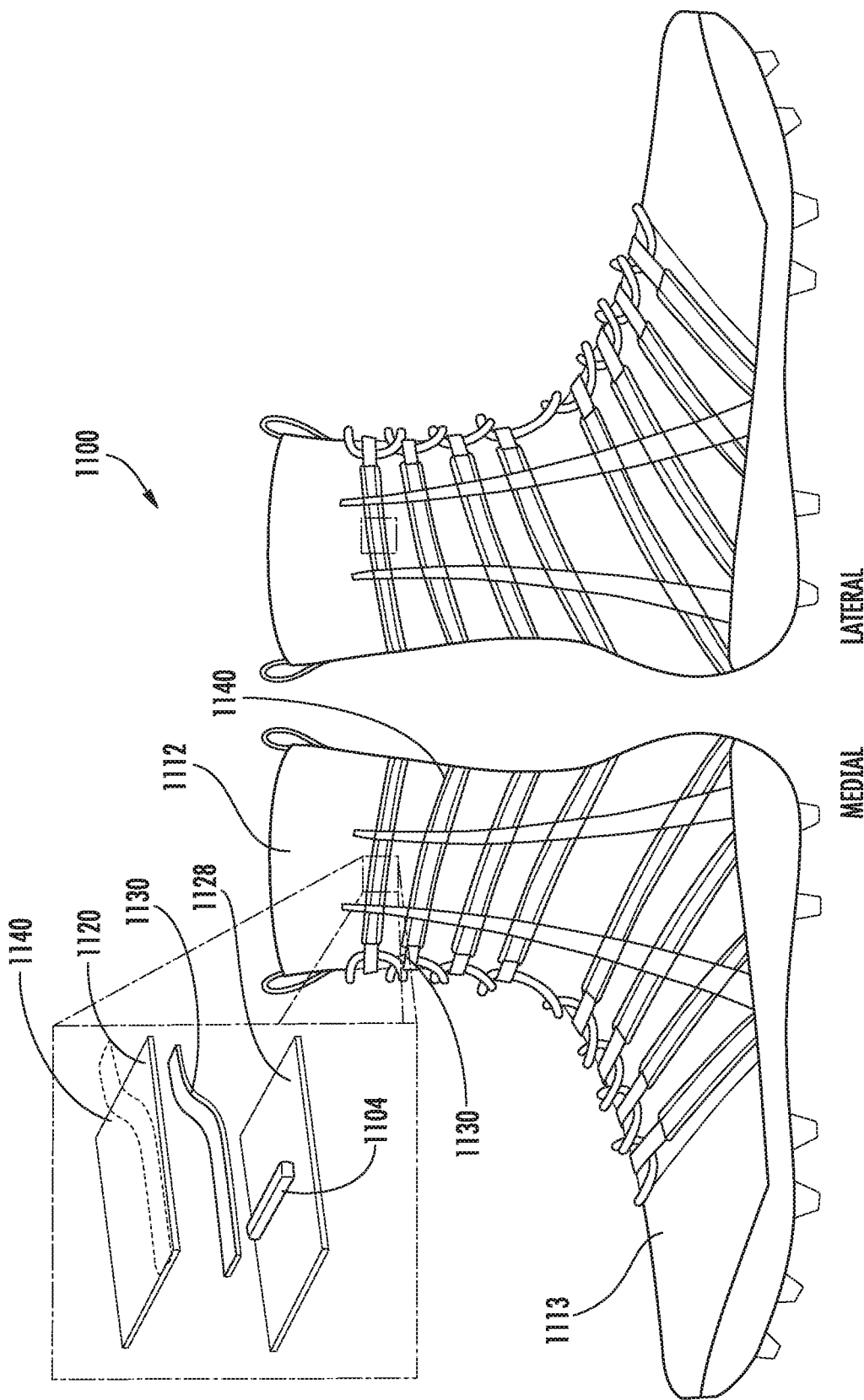
FIG. 11 is a cutaway side view of the medial and lateral sides of an alternative article of footwear illustrating channels that enable movement of tensioning members depicted in FIG. 9.

FIG. 11 depicts another alternative embodiment of an article of footwear, depicted here as a partial cutaway view of a cleat 1100 that includes support members integrated with an inner layer 1112 and channels such as channel 1140 to guide tensioning members 1130. Inner layer 1112 is positioned inside of an outer shell 1113. Cleat 1100 includes support members 1104 that are similar to the vertical support members 100 seen in FIG. 9-10. As shown in FIG. 11, the cleat 1100 may include one or more channels 1140 formed in the inner layer 1112 to enable movement of one or more of the tensioning members 16 described above. The inner layer 1112 further includes a top layer 1120 and bottom layer 1128. Both the top layer 1120 and bottom layer 1128 are formed from a stretchable materials such as compression fabrics, polypropylenes, webbing, neoprene, elastane, synthetics, and the like. The channel 1140 is stitched into the top layer 1120 of the inner layer 1112. The channel 1140 corresponds to the shape and configuration of one of the tensioning members in the cleat 1110, exemplified by tensioning member 1130. The tensioning member 1130 is arranged over one or more of the support members, such as vertical support 1100, and under the channel 1140 in the top layer 1120. In operation, the channel 1140 enables the tensioning member 1130 to tighten and loosen without interference from the outer shell 1113. Multiple channels such as channel 1140 may also prevent fouling or tangling of different tensioning members in operation. While FIG. 11 depicts a cleat 1100 that includes vertical support members 1100, a similar embodiment may include vertical and horizontal support members as well.

Article of Footwear with Adjustable Stabilizing Members

In another alternative footwear embodiment, one or more adjustable stabilizing members are positioned within the footwear to provide additional stability to one or more portions of a foot that is inserted in the footwear. FIG. 12A-FIG. 12E depict an inner layer 1212 of footwear 1200 that includes stabilizing members 1202 that provide stability to portions of the foot. The stabilizing members 1202 and are held in place using one or more tensioning members 1215, embodied here as flexible straps 1208 and 1220A-1220B. The stabilizing members 1202 are repositionable members placed between an inner layer 1212 and outer layer (omitted for clarity) inside of the foot cavity of an article of footwear. Each stabilizing member 1202 is configured to conform to one or more regions of the foot, such as the heel or ankle. One or more of the tensioning members 1215 engages each stabilizing member 1202 to enable the user to adjust the stabilizing member 1202 with respect to a foot in the footwear. One end of each tensioning member 1215 extends outside of the foot cavity and outer shell of the footwear, and may be secured in position after tension is applied. Thus, the user may tighten, loosen, or otherwise adjust the fit of each stabilizing member 1202 to the foot by tightening and loosening a tension member 1215 in a similar manner to the tensioning members 16 described above.

Figure 12C:
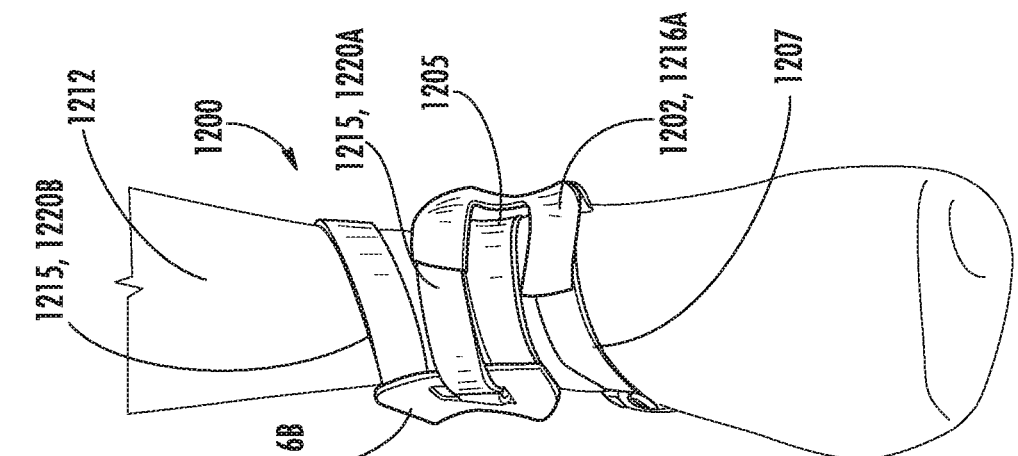
FIG. 12C is an anterior view of the inner layer and stabilizing member for an ankle depicted in FIG. 12A-FIG. 12B.
Figure 12B:
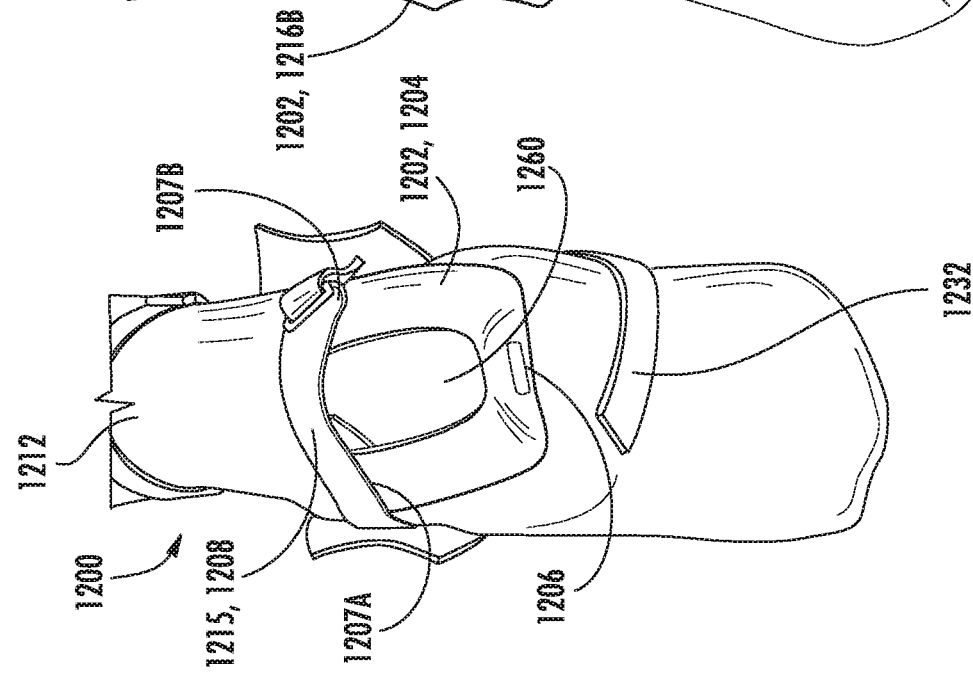
FIG. 12B is lower posterior perspective view of the inner layer and stabilizing member for a heel depicted in FIG. 12A.
Figure 12A:
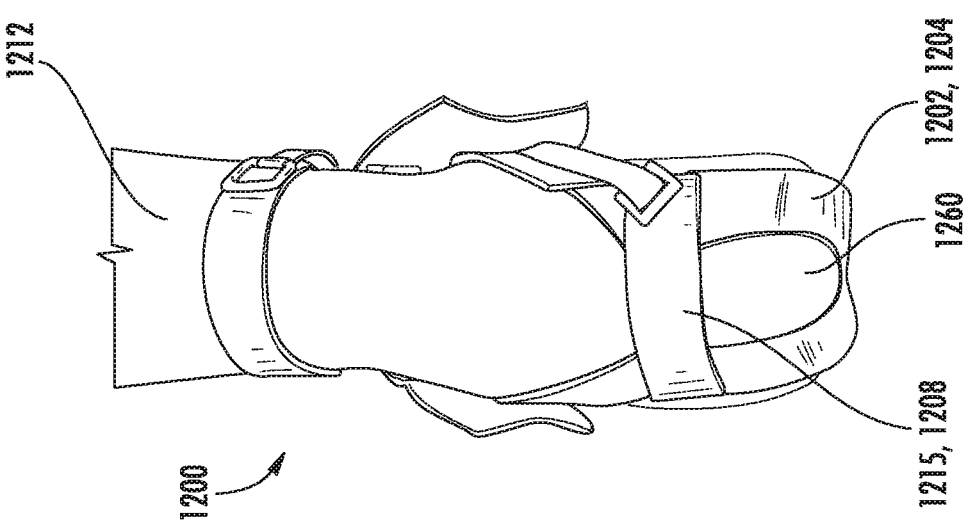
FIG. 12A is a posterior view illustrating an inner layer and stabilizing member for a heel in an article of footwear.

FIG. 12A and FIG. 12B depict an inner layer 1212, heel stabilizing member 1204, and tensioning member 1208, seen here as a tensioning strap. Heel stabilizing member 1204 has a shape that conforms to the heel 1260 of a foot placed in the inner layer 1212, and the stabilizing member 1204 is positioned behind the heel. The heel stabilizing member 1204 has a U-shaped configuration with a lower end 1206 positioned at the base of the heel 1260 and two upper ends 1207A and 1207B that extend toward the ankle. Alternative configurations of the heel stabilizing member 1204 may include different shapes that provide stability to the heel 1260. The lower end 1260 is affixed to the inner layer 1212. The upper ends 1207A and 1207B engage the tensioning member 1208 around the lateral and medial sides of the posterior of the heel 1260. The tensioning member 1208 may be fixedly attached to the upper ends 1207A and 1207B of the stabilizing member 1204, or may thread through openings formed in the upper ends 1207A and 1207B of the stabilizing member 1204.

The tensioning member 1208 includes one end 1232 that is attached to the inner layer 1212 under the sole of the foot. The length of the tensioning member 1208 may be fixedly attached or threaded through the ends 1207A and 1207B of the stabilizing member 1204. A second end of the tensioning member 1236 may end in a tension adjustment member, such as a tab or other attachment device that is configured to engage a fastening pad or other fastening mechanism positioned on the outside of the footwear in a similar manner to the embodiments of FIG. 1A-FIG. 8.

Figure 12E:
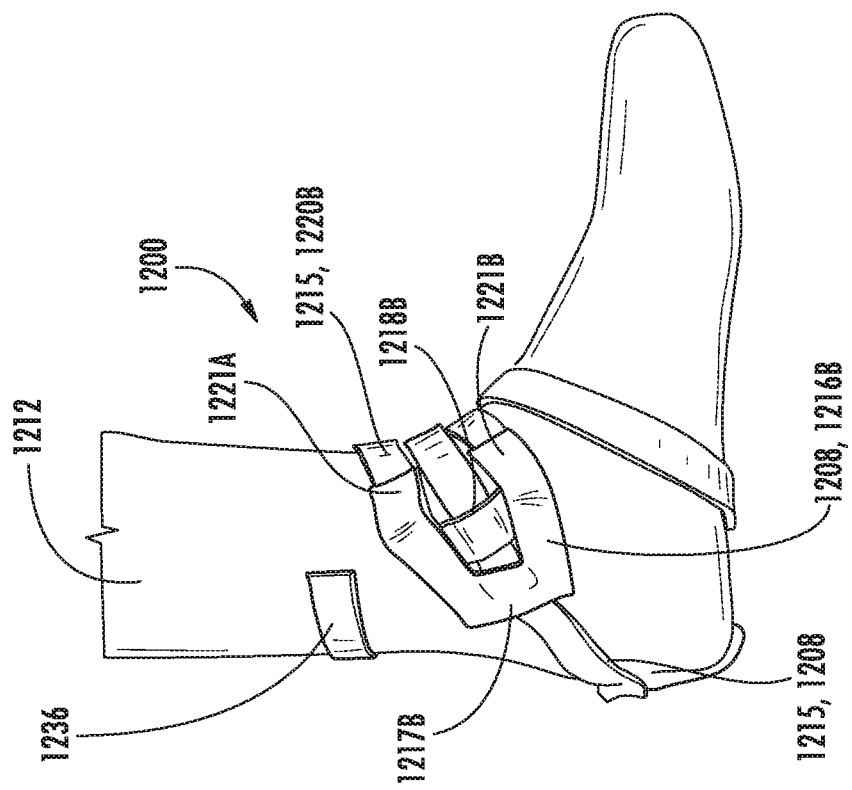
FIG. 12E is a lateral side view of an inner layer and stabilizing member for an ankle in the article of footwear depicted in FIG. 12A-FIG. 12D.
Figure 12D:
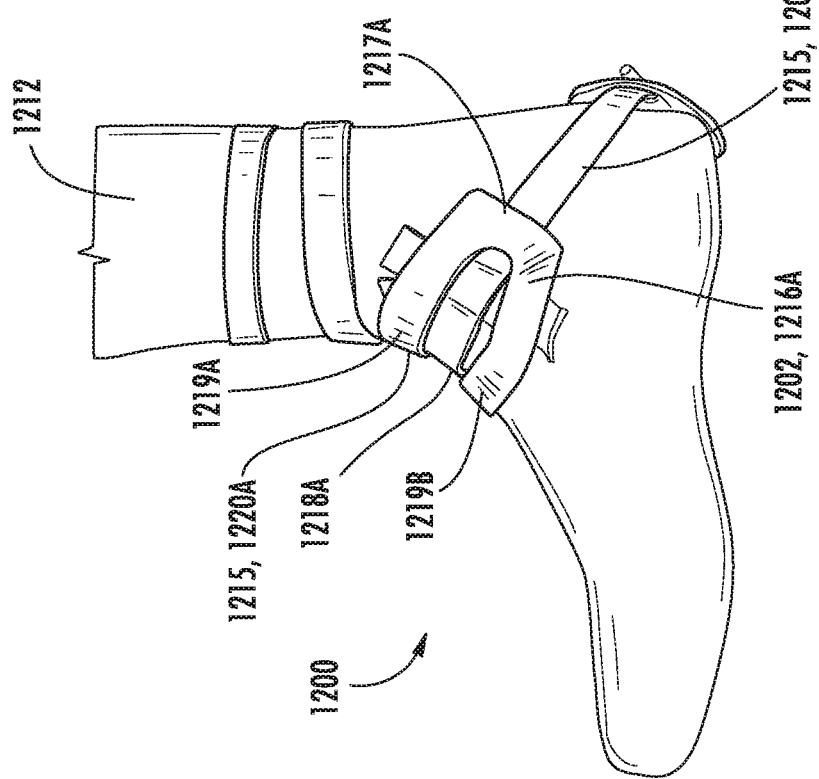
FIG. 12D is a medial side view of the article of footwear depicted in FIG. 12A-FIG. 12C illustrating the position of an ankle stabilizing member.

FIG. 12C-FIG. 12E depict two ankle stabilizing members 1216A and 1216B that conform to the medial side and lateral side, respectively, of an ankle. Both of the ankle stabilizing members 1216A and 1216B are formed with a U-shape. As seen in FIG. 12C and FIG. 12D, a curved end 1217A of the U-shaped stabilizing member 1216A is positioned to engage the posterior side of the medial malleolus 1218A. The curved end 1217A is affixed to the inner layer 1212. The open ends 1219A and 1219B of the stabilizing member 1216A extend above and below the medial malleolus, respectively, toward the anterior of the foot. The end 1219A of the ankle stabilizing member 1216A engages one end of a tensioning member 1220A. The tensioning member 1220A has a length that extends outside of the article of footwear to a second end. The user may pull on the second end of the tensioning member 1220A or on a tension adjustment member affixed thereto in order to adjust the ankle stabilizing member 1216A. The end 1219B of the ankle stabilizing member 1216A engages a strap 1207 that is affixed to the lateral side of the inner layer 1212.

As seen in FIG. 12C and FIG. 12E, a curved end 1217B of the U-shaped ankle stabilizing member 1216B is positioned to engage the posterior side of the lateral malleolus 1218B. The curved end 1217B is affixed to the inner layer 1212. The open ends 1221A and 1221B of the stabilizing member 1216B extend above and below the lateral malleolus, respectively, toward the anterior of the foot. The end 1221A of the ankle stabilizing member 1216A engages one end of a tensioning member 1220B. The tensioning member 1220B has a length that extends outside of the article of footwear to a second end. The user may pull on the second end of the tensioning member 1220B or on a tension adjustment member affixed thereto in order to adjust the ankle stabilizing member 1216B. The end 1221B of the ankle stabilizing member 1216B engages a strap 1205 that is affixed to the medial side of the inner layer 1212.

In a finished article of footwear, an outer shell, omitted in FIG. 12A-FIG. 12E for clarity, encloses the stabilizing members 1204, 1216A and 1216B. The stabilizing members 1204, 1216A, and 1216B are not directly attached to the outer shell to enable adjustment of the semi-rigid members. The stabilizing members 1204, 1216A, and 1216B are each formed from one or more semi-rigid materials to enable the stabilizing members to conform to the foot and ankle while resisting ankle rolls and other movements that may cause injuries. As used herein, the term "semi-rigid" refers to a material that resists deformation under stress, but deforms in response to a sufficient force and then returns to an undeformed state when the force is removed. Common examples of semi-rigid materials include polymeric materials such as polyimides and thermoplastics. The stabilizing members depicted in FIG. 12A-12E may be incorporated into any of the footwear embodiments and modifications thereof described in this application.

In operation, a user inserts the foot inside the inner layer 1212 located in the foot cavity to enable the heel 1260 to engage the stabilizing member 1204 and the ankle to engage the stabilizing members 1216A and 1216B. The user may first apply a selected tensioning force to the end of the tensioning member 1208 that extends outside of the footwear to draw the stabilizing member 1204 into further engagement with the heel 1260 to provide support to the heel 1260 when wearing the footwear. As described above, the tensioning member 1208 may be tightened or loosened to increase or decrease, respectively, the tightness of the stabilizing member 1204 with respect to the foot. The tensioning member 1208 is secured to an outer shell of the footwear in a similar manner to the embodiments of FIG. 1-FIG. 8 to retain the stabilizing member 1204 in the selected position.

After adjusting the tensioning member 1208 and associated heel stabilizing member 1204, the user may then adjust the tensioning members 1220A and 1220B that engage ankle stabilizing members 1216A and 1216B, respectively. To accomplish this, the user applies a selected tensioning force to the ends of tensioning members 1220A and 1220B that extend outside of the footwear and secures them to the outer shell to engage the stabilizing members 1216A and 1216B, respectively, to the ankle. The foregoing description does not limit the order of adjusting the tensioning members 1215 and stabilization members 1202. The user may adjust the tensioning members 1208, 1220A, and 1220B and corresponding stabilization members 1204, 1216A and 1216B in any order.

The stabilizing members 1204, 1216A, and 1216B provide additional support to the heel and ankle. The tensioning members 1215 enable a user to adjust the stabilizing members 1202 to conform to the foot and ankle while wearing the footwear. While the foregoing embodiments depict stabilizing members 1202 engaging the heel and ankle regions of the foot, alternative embodiments may have stabilizing members for one of the heel and ankle, and may include similar stabilizing members that engage other areas of the foot.

Article of Footwear with a Locking Strap

Figure 13:
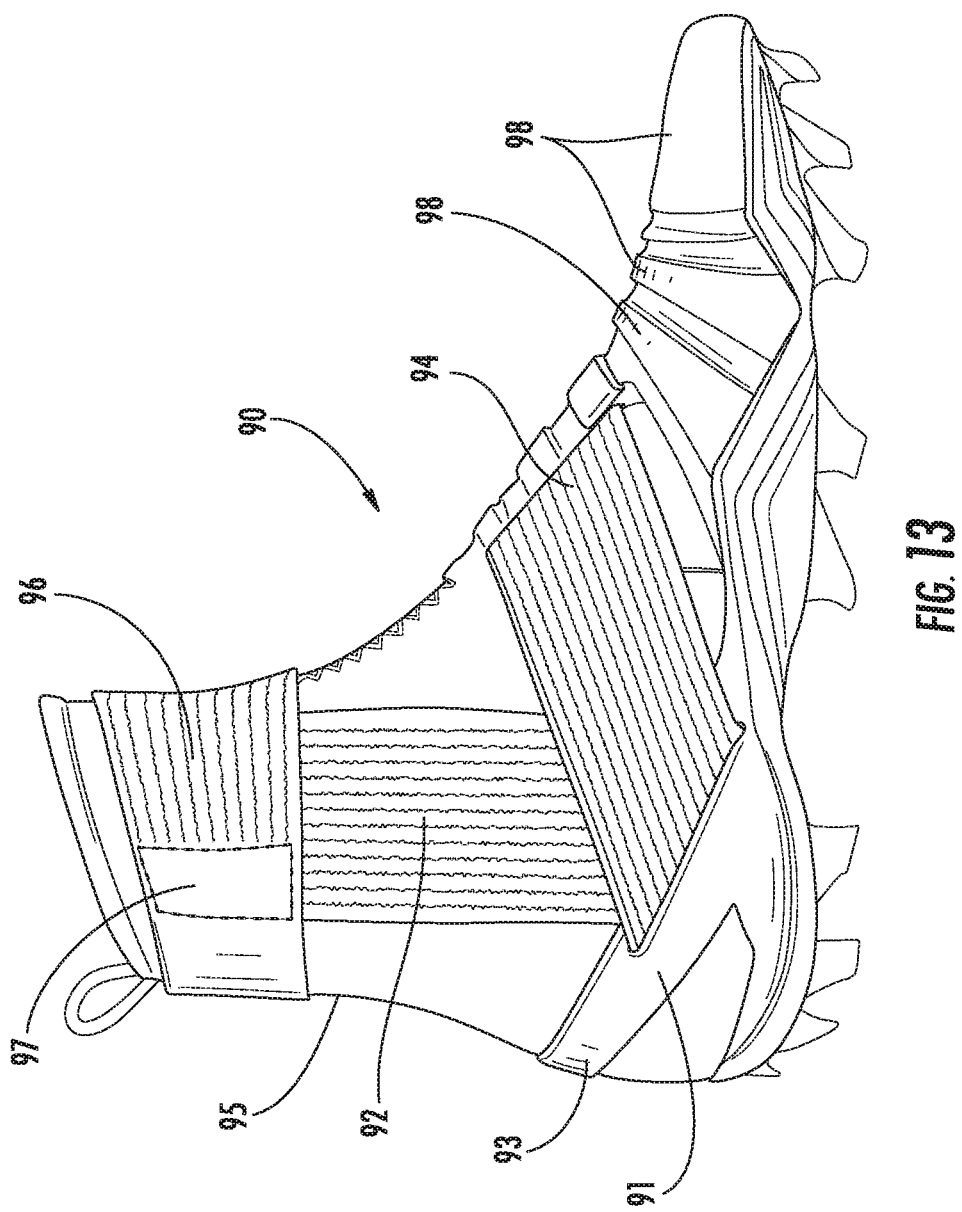
FIG. 13 is a partial cutaway view of an alternative embodiment of the article of footwear of FIG. 1A illustrating an alternative tensioning strap arrangement.

FIG. 13 illustrates an alternative embodiment of a cleat 90 that includes a locking strap 96 for securing a tensioning strap 92 in place after a user adjusts the tensioning strap to apply compression to a foot inserted into the cleat 90. Cleat 90 includes tensioning strap 92 positioned in the foot cavity, shown here in a partial cutaway view, that is attached at an attachment point 94 in proximity to the forefoot or midfoot region of the cleat 90. Cleat 90 also includes a locking strap 96 positioned on an outer shell 95 of the cleat 90. The locking strap 96 includes a first end that is affixed to the outer shell 95. The locking strap 96 wraps around the ankle region of a foot inserted into the cleat 90, to surround an end of the tensioning strap 92 or a tensioning member affixed to the end of the tensioning strap 92 that extends out of the outer shell 95. A second end 97 of the locking strap 96 is configured to be releasably secured to another portion of the locking strap 96 using a hook and loop material. Alternative embodiments may include various other fastening mechanisms that secure the second end 97 of the locking strap 96 in place.

The cleat 90 also includes a toe guard 98. Toe guard 98 may comprise a material with an increased resistance to compression forces, such as those experiences when a large load is placed thereupon. Such materials exhibit a higher modulus of elasticity and include, but are not limited to, Kevlar fibers, plastics, and the like.

In operation, a user first inserts a foot into cleat 90. The user then pulls on an end of tensioning strap 92 that extends out of the outer shell 95 to apply a tensile force to the tensioning strap 92. Such application urges the heel of a foot inserted into the cleat 90 into the heel region 91 of the cleat 90. The heel region 91 may include an external support member 93 that engages with the posterior end of the heel. The end of the tensioning strap 92 is secured to the outer shell 95 of the cleat 90 using a hook and loop type of engagement (although other known methods may also be used). The user then wraps locking strap 96 around the ankle region of the foot and the end of the tensioning strap 92. After the locking strap 96 is wrapped around the foot, the user fastens the second end 97 of the locking strap. The locking strap 96 enables the tensioning strap 92 to remain in a position with the tensile force applied after the user tightens the tensioning strap 92.

Article of Footwear with Serially Arranged Tensioning Members

Figure 14:
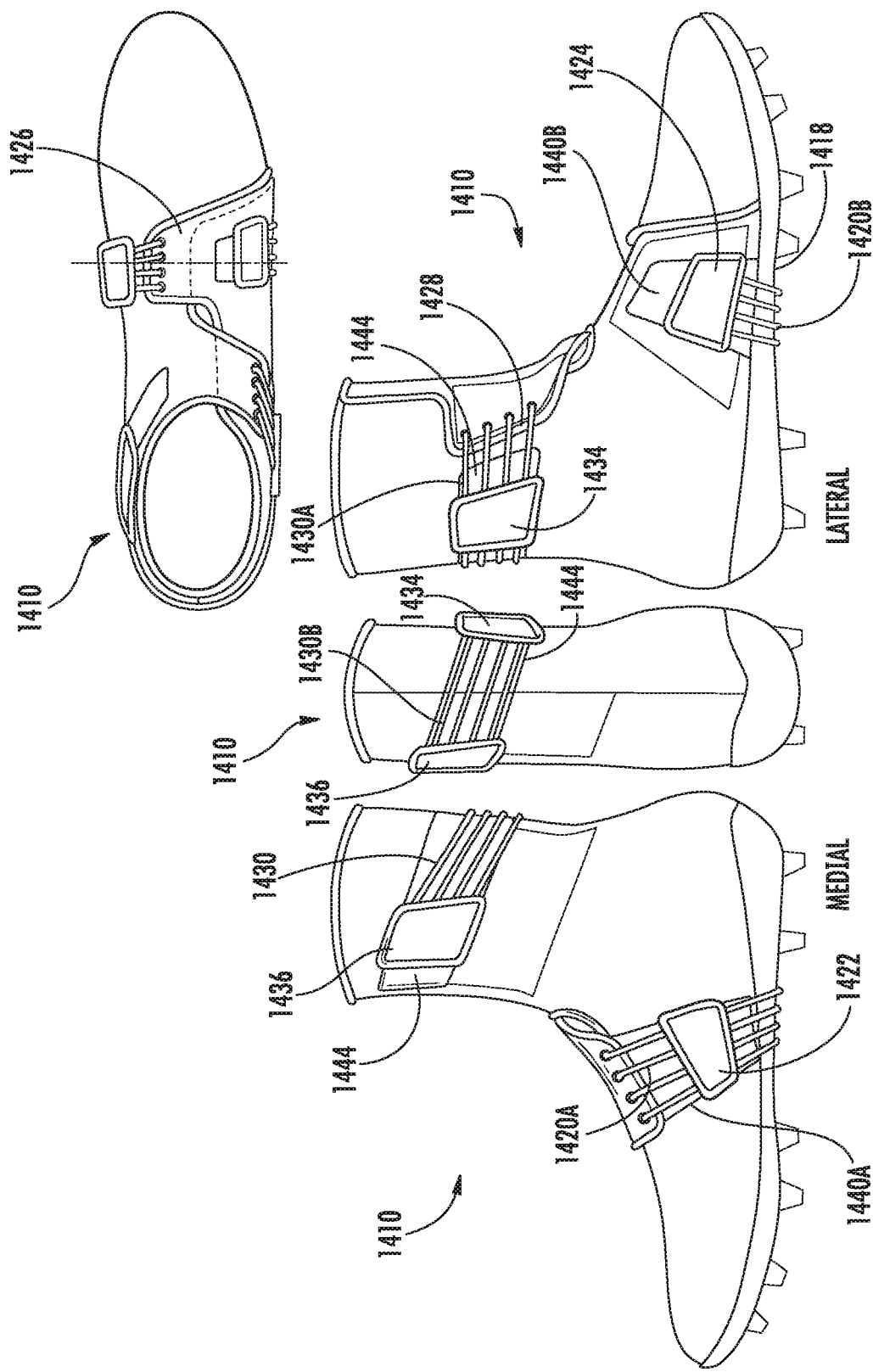
FIG. 14 is a partial cutaway view illustrating an alternative arrangement of tensioning members in an article of footwear.

FIG. 14 depicts four views of another embodiment of an article of footwear 1410 that includes tensioning members engaged in series with adjustment tabs. In the embodiment of FIG. 14, a first set of tensioning members 1420A engage the mid foot region extending from a midfoot flap 1426 on the medial side of the footwear 1410 to a tab 1422 positioned on the medial side of the footwear 1410. A second set of tensioning members 1420B extend from the tab 1422 underneath the sole 1418 to another tab 1424 that engages a fastening pad 1440A on the lateral side of the footwear. In a similar arrangement, a first set of tensioning members 1430A extend from a flap 1428 on the lateral side of the footwear 1410 and extend to a first tab 1434 that may be secured to a fastening pad 1444. A second set of tensioning members 1430B extend from the first tab 1434 around the posterior of the ankle to another tab 1436 that is secured to the fastening pad 1444 on the lateral side of the foot. In the embodiment of FIG. 14, fastening pad 1444 wraps around the posterior of the footwear 1410 to fasten flaps 1434 and 1436 on both the lateral and medial side of the footwear 1410. An alternative embodiment may include separate fastening pads on the medial and lateral sides. Flaps 1426 and 1428 may overlap each other.

In operation, a user inserts a foot into the footwear 1410. The user tightens tensioning members 1420A by pulling on the tab 1422, and then secures the tab 1422 to a medial fastening pad 1440A. The user then tightens tensioning members 1420B by pulling on the tab 1424 and securing the tab 1424 to a lateral fastening pad 1440B. In a similar manner, the user may adjust tab 1434 first followed by tab 1436 to adjust the tensioning members 1430A and 1430B, respectively. The magnitude of compressive force applied to the foot by tensioning members 1420A and 1430A may be different than the compressive force applied by tensioning members 1420B and 1430B, respectively. The configuration of footwear 1410 provides compression to the medial and lateral sides of a foot without a crisscross arrangement of the tensioning members 1430A and 1430B.

Article of Footwear with Tensioning Members Affixed to a Strap

FIG. 15 depicts a medial and lateral view of another embodiment of an article of footwear 1510 that includes tensioning members that are attached to a strap. Footwear 1510 includes tensioning members 1520 that are attached to an inner layer 1512 near the heel of the foot. The tensioning members 1520 are attached to one end of a strap 1530 that wraps around the ankle and is configured to be fastened to the footwear 1510 at a location above the ankle. The strap 1530 is attached the tensioning members 1520 at a location between the inner layer 1512 and an outer shell 1513, with the other end of the strap 1530 extending to the outside of the outer shell 1513. The strap 1530 has a width that enables each of the tensioning members 1520 to be attached to one end of the strap 1530. The strap 1530 is positioned within a sleeve 1516 formed outside of the inner layer 1512. The sleeve 1516 enables the strap 1530 to be tightened and loosened in operation. The strap 1530 may be attached to tensioning members on either the medial or lateral side of the foot, and may wrap around the foot and ankle one or more times.

In operation, a user inserts a foot into the footwear 1510. The user pulls on the end of the strap 1530 that extends outside of the outer shell 1513. The tensioning members 1520 apply a compressive force to the heel, and the strap 1520 applies a compressive force to the ankle. The tensioning members 1520 are shown as engaging the heel, but may engage the forefoot and midfoot regions as well.

Article of Footwear with Tensioning Strap and Support Members

Figure 16:
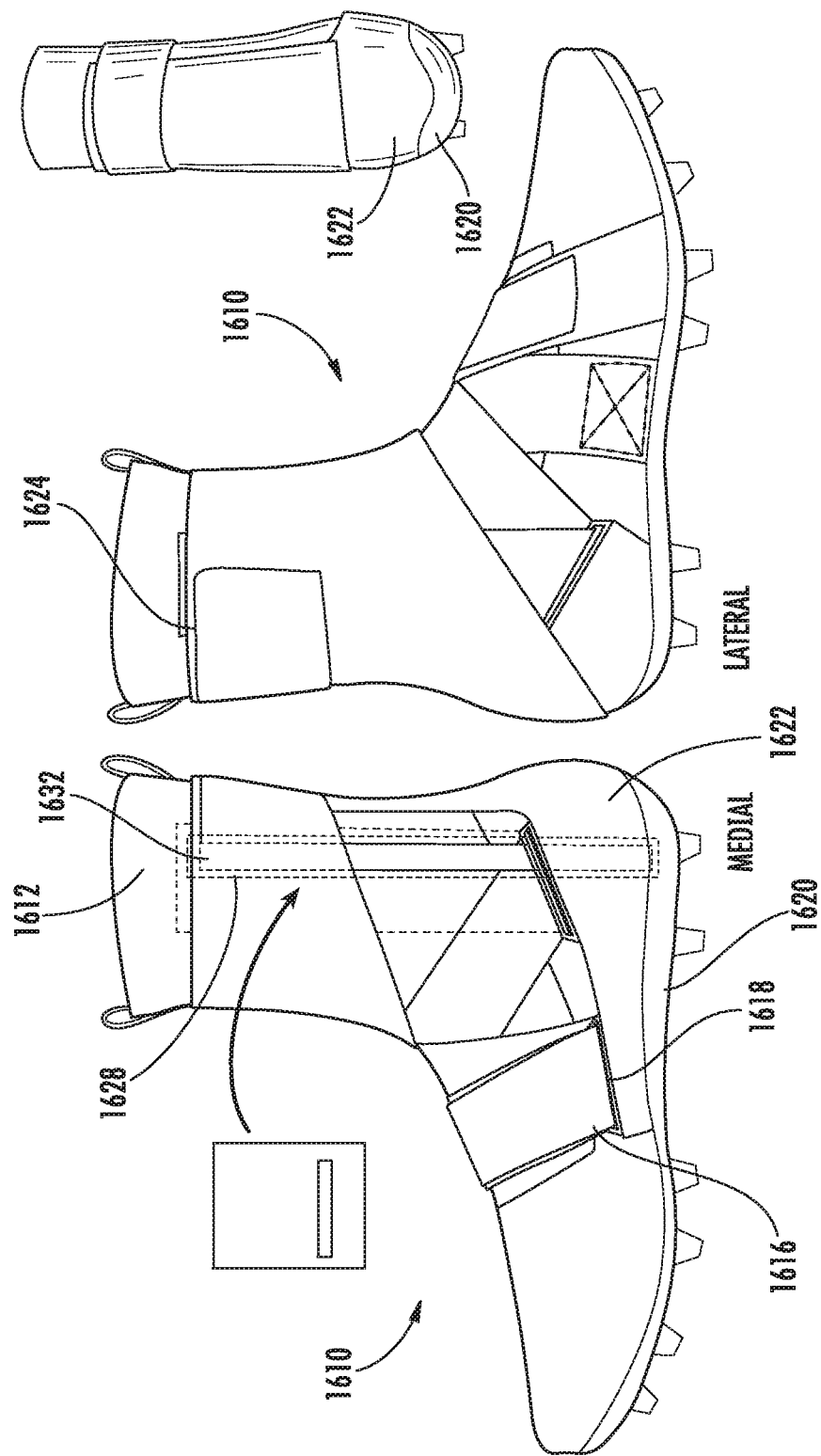
FIG. 16 is an illustration depicting the positions of tensioning straps and a support member in another alternative embodiment of an article of footwear.

FIG. 16 depicts another alternative embodiment of an article of footwear 1610 including tensioning straps and a support member. Article of footwear 1610 has an inner layer 1612, with a strap 1616 that attached to the lateral side of the inner layer 1612. The strap 1616 extends over the fore foot region through a D-ring 1618 on the medial side of the footwear 1610. The strap 1616 extends back to the lateral side of the footwear 1610, where an end of the strap 1616 may be fastened to the exterior of the footwear 1610. A second strap 1622 includes one end attached to the upper edge of the sole 1620 around the forefoot, midfoot, and heel portions of the sole 1622. Strap 1622 extends around the upper foot and wraps around the ankle in the footwear 1610. The strap 1622 includes one end 1624 that extends outside of an outer shell of the footwear 1610 to enable tightening and loosening of the strap 1620.

Footwear 1610 includes one or more pockets 1628 formed in the inner layer 1612. A support member, embodied herein as a nylon support member 1632 is positioned within the pocket 1628. The pocket 1628 is configured to enable the support member 1632 to move within the pocket 1628. In the example of FIG. 16, the pocket 1628 is configured with a length and a width that are 6 mm larger than the corresponding length and width of the support member 1632. Strap 1622 wraps around the pocket 1628 and support member 1632.

In operation, a user inserts a foot into the footwear 1610. The user may pull on straps 1616 and 1622 to apply compression to the forefoot, midfoot, heel, and ankle regions of the foot. Tension may be applied to the straps 1616 and 1622 in any order. The support member 1632 may move within the pocket 1628 to provide support to the foot in different orientations when wearing the footwear 1610.

Article of Footwear with Tensioning Strap Wrapped Around Foot

Figure 17:
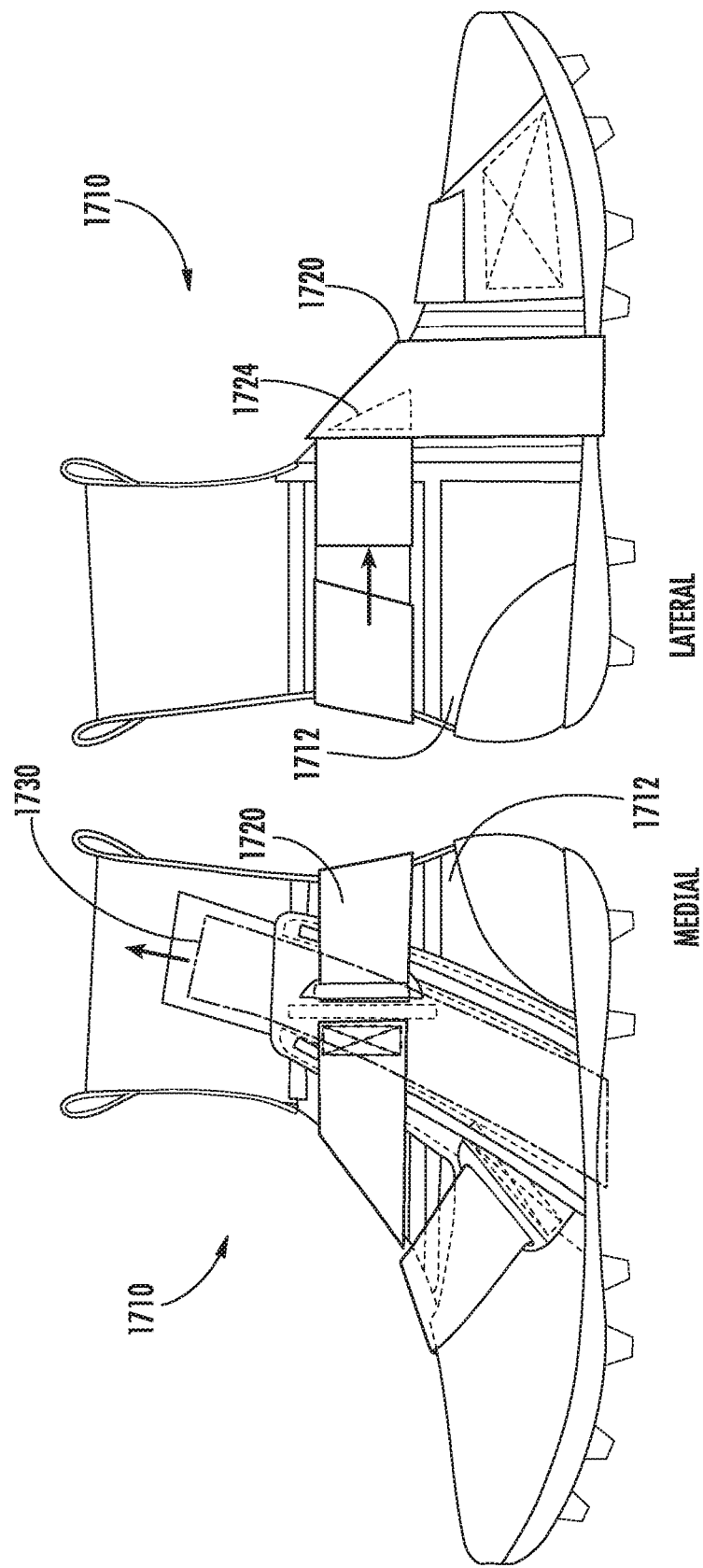
FIG. 17 is an illustration of a tensioning strap in a medial side and lateral side of an alternative embodiment of an article of footwear.

FIG. 17 depicts another alternative embodiment of an article of footwear 1710 including a tensioning strap 1720 that is configured to pass under the foot and around the ankle. Tensioning strap 1720 is attached to an inner layer 1712 of the footwear at a midfoot location 1724 on the lateral side of the footwear 1710. The tensioning strap 1720 extends horizontally along the lateral side of the footwear 1710, wraps around the medial side of the footwear 1710, and returns to the midfoot region on the lateral side of the footwear 1710. The tensioning strap 1720 further extends down the lateral side of the footwear 1710, under the foot, and extends up the medial side of the footwear 1710 where an end 1730 is positioned outside of an outer shell of the footwear 1710. The end 1730 may be fastened to the outer shell of the footwear 1710.

In operation, a user inserts a foot into the footwear 1710. The user may pull on the strap 1720 to apply compression to the midfoot and ankle regions of the foot. In the embodiment of FIG. 17, a single strap 1720 applies compression to both the medial and lateral sides of the foot. While the strap 1720 is depicted as being attached to the lateral side of the footwear 1710 and extending through the medial side of the footwear 1710, and alternative configuration may arrange a tensioning strap to extend from the medial side to the lateral side.

Article of Footwear with Internal Compression Wrap

Figure 18A:
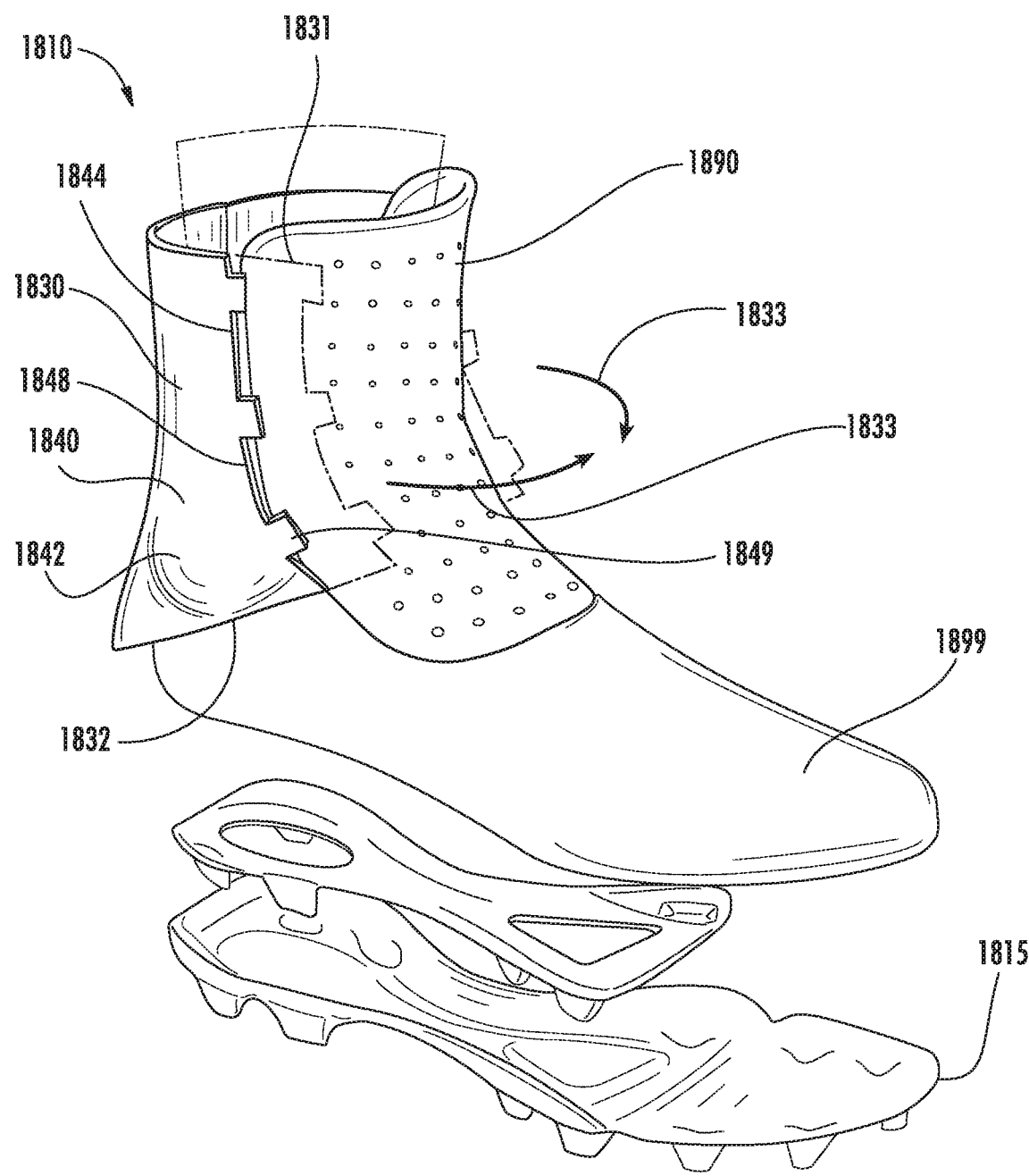
FIG. 18A is an illustration of an alternative embodiment of an article of footwear including an elastic wrap member positioned in the foot cavity.
Figure 18B:
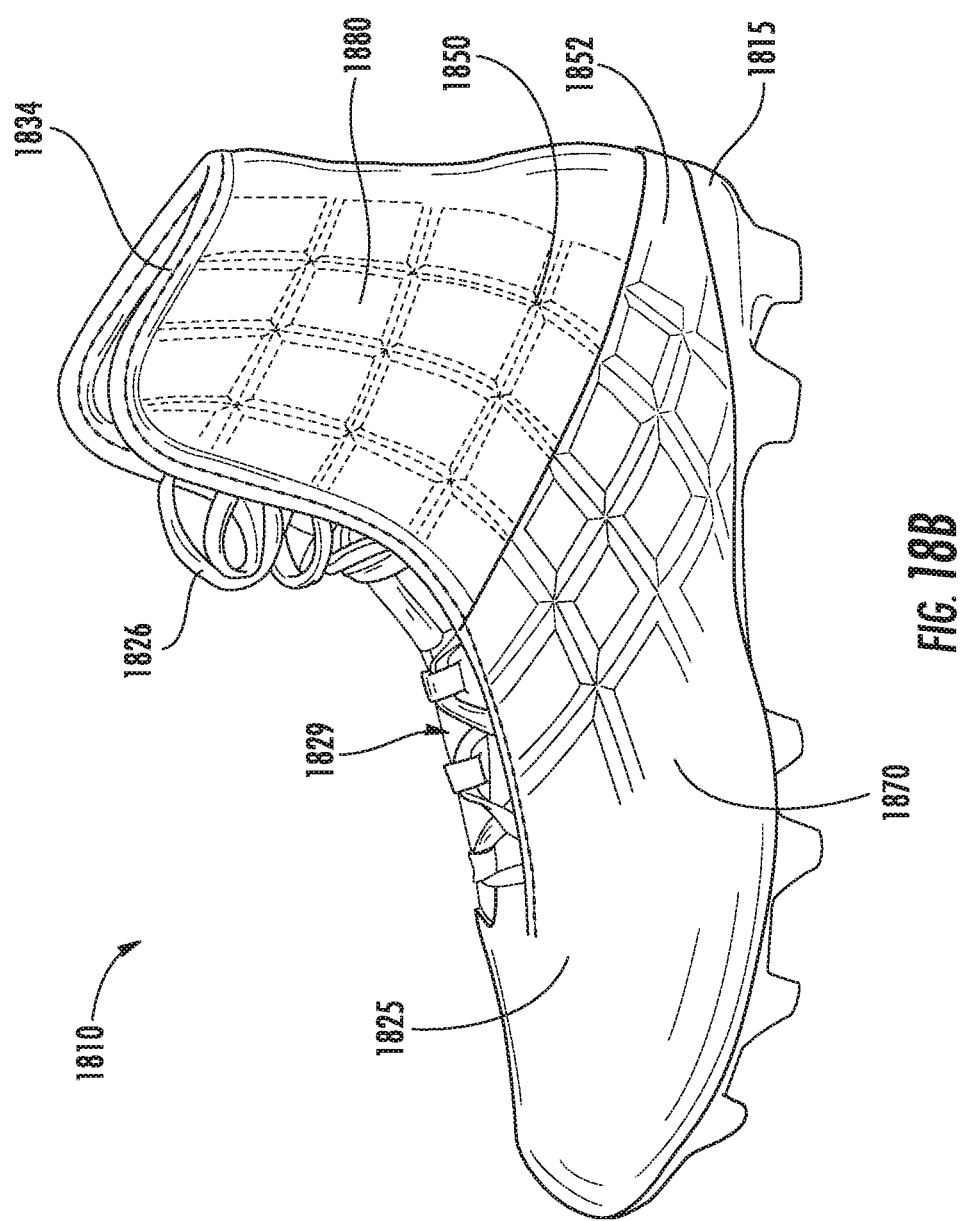
FIG. 18B shows a side view of the article of footwear of FIG. 18A.
Figure 18C:
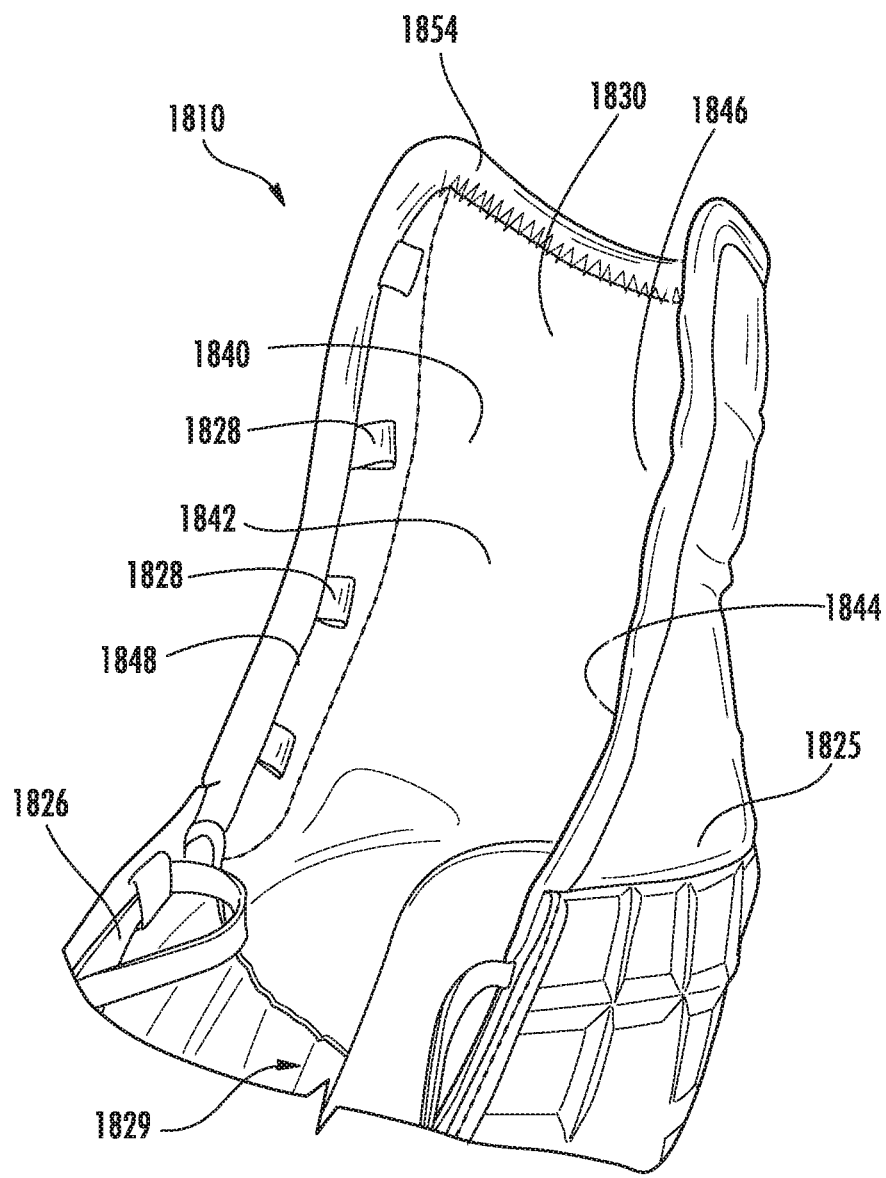
FIG. 18C shows a perspective view of the foot cavity of the article of FIG. 18A with the elastic wrap member positioned in the foot cavity.

FIGS. 18A-18C depict another alternative embodiment of an article of footwear 1810 including a sole 1815 connected to a shoe upper 1825 (not shown in FIG. 18A, see FIGS. 18B and 18C), and an elastic wrap member 1830 positioned within the foot cavity. In this embodiment, the sole 1815 is provided as a cleat, and the shoe upper 1825 is provided in the form of an athletic boot. The elastic wrap member 1830 is provided as a sheet of stretchable material within the foot cavity which acts as a cradle member to partially surround the foot 1899 of the wearer and provide compression to the foot 1899 of the wearer.

The elastic wrap member 1830 is comprised of an elastic fabric material similar to that commonly found in traditional ankle wraps. The material used to form the elastic wrap member 1830 includes a resilient stretchable component that allows the elastic wrap member 1830 to be stretched around a wearer's foot when tightened within the foot cavity, and then spring back to its original shape when loosened within the foot cavity. Accordingly, the elastic material may be provided as a woven fabric material that includes elastane or other elastic fibers. The elastic material may also include non-elastic fibers or less elastic fibers such as polyester, nylon or cotton fibers.

In the embodiment of FIGS. 18A-18C the elastic wrap member 1830 is located in an ankle region 1850 of the article of footwear 1810. In particular, the elastic wrap member 1830 is positioned within the foot cavity such that a lower edge 1832 of the elastic wrap member 1830 is located in a heel region 1852 of the article of footwear 1810. The elastic wrap member 1830 extends up from the heel region 1852, over the ankle region 1850, and to a top edge 1854 of the article of footwear 1810. Accordingly, the elastic wrap member 1830 at least partially or completely covers the ankle of the wearer when the wearer's foot 1899 is positioned within the article of footwear.

In the embodiment of FIGS. 18A-18C, the elastic wrap member 1830 includes a generally cradle portion 1840 and adjustable edges 1848. The cradle portion 1840 forms a C-shaped cylindrical member that extends along the interior of the shoe upper 1825. The cradle portion 1840 includes a main body 1842 that is generally free-floating within the foot cavity and therefore generally separate from the shoe upper 1825. However, although the main body 1842 is generally separate from the shoe upper 1825, relatively small sections of the cradle portion 1840 may be fastened to the shoe upper 1825 at various locations, including along a forward seam 1844 that runs along the tongue slot on the shoe upper 1825. In other embodiments, additional portions of the main body 1842 of the cradle portion 1840 may also be fastened to the shoe upper 1825 in addition to the forward seam 1844. For example, as best shown in FIG. 18C, the main body 1842 of the cradle portion 1840 may be connected to the shoe upper 1825 along a vertical seam 1846 in the rear of the shoe upper 1825. These seams 1846, 1844 that fasten the cradle portion 1840 to the shoe upper 1825 may be provided using any of various means, such as stitching, adhesives, or other fastening means. However, even with the seams 1842, 1844, most of the main body 1842 of the cradle portion 1840 remains generally free-floating and moveable relative to the shoe upper 1825. This includes the portions between the vertical seam 1846 and the forward seam 1844 of the cradle portion 1840. Because substantial portions of the main body 1842 are free-floating relative to the shoe upper 1825, the cradle portion 1840 may be tightly wrapped around the foot 1899 of the wearer even if the shoe upper is not as tightly wrapped around the foot 1899.

The adjustable edges 1848 of the elastic wrap member 1830 are generally connected to the portion of the shoe upper 1825 that includes the shoelace eyelets 1828 for the article of footwear 1810. Accordingly, the adjustable edges 1848 of the elastic wrap member 1830 may be connected to the shoe upper 1825 along the above-mentioned forward seams 1842. However, in other embodiments, the adjustable edges 1848 may be coupled to other portions of the shoe upper, such as only the shoelace eyelets 1828. As shown in FIG. 18A, the adjustable edges 1848 may include tab members 1849 that extend the elastic wrap member 1830 to the shoelace eyelets 1828 on the shoe upper 1825. In some embodiments, the forward seam 1844 of the cradle portion 1840 does not extend to the shoelace eyelets 1828 on the shoe upper 1825, but may be fastened to other areas on the shoe upper 1825. For example, the forward seam 1844 of the cradle portion 1840 may extend along the tongue slot 1829 or other line that follows the eyelets 1828 on the shoe upper 1825.

As described above, in the embodiment of FIGS. 18A-18C, the elastic wrap member 1830 only partially surrounds the ankle of a wearer from the rear of the ankle (i.e., the Achilles tendon area) to a position forward of the ankle. For added support on the anterior portion of the ankle, the tongue 1890 may be provided as a thick padded member. For example, the tongue 1890 may be a custom molded open cell foam product that is flexible and provides cushioned support on the anterior portion of the foot, as shown in FIG. 8A. In some embodiments, the tongue 1890 may include various surface patterns or other features.

In operation, a wearer inserts his or her foot 1899 into the foot cavity of the article of footwear 1810 and pulls the ends of the shoe laces 1826. This action draws the shoelace eyelets 1828 and related upper perimeter portions of the shoe upper 1825 together in a traditional fashion. Because the elastic wrap member 1830 is coupled to the shoe upper along the eyelets or other upper perimeter portions, pulling the shoe laces 1826 also pulls the elastic wrap member 1830 around the foot 1899 of the wearer, as illustrated by arrows 1833 in FIG. 18A. This results in the elastic wrap member 1830 being drawn to a stretched position as indicated by dotted lines 1831 in FIG. 18A. Accordingly, the elastic wrap member 1830 provides a convenient ankle wrap or other foot wrap that is integrated into the article of footwear 1810 without the need for a separate wrap member.

With particular reference now to FIG. 18B, in at least one embodiment, the outer shell of the shoe upper 1825 includes a non-elastic portion 1870 and an elastic portion 1880. A seam 1875 may be formed on the article of footwear 1810 where the elastic portion 1880 meets the non-elastic portion 1870 of the shoe upper. The non-elastic portion 1870 is formed from more traditional materials for a shoe upper, such as leather, synthetic leather, or a soft plastic material. The elastic portion 1880 of the shoe upper 1825 comprises an elastic material with resilient qualities, similar to the elastic wrap member 1830. In at least one embodiment, the elastic portion 1880 is comprised of a foam material adhered to one or more layers of elastic fabric. For example, the elastic portion 1880 may include an open cell foam that is sandwiched between two layers of stretch fabric comprised of elastane or other stretch material.

The non-elastic portion 1870 of the article of footwear is positioned in a midfoot region and a forefoot region of the shoe upper 1825. The elastic portion 1880 is generally provided on the same portion of the article of footwear 1810 where the elastic wrap member 1830 is located (e.g., the ankle portion 1850). Because the elastic portion 1880 of the shoe upper 1825 is both flexible and elastic, the elastic portion 1880 is allowed to more closely adhere to the foot 1899 of the wearer when the shoelaces 1826 are tightened on the article of footwear 1810. Moreover, the combination of the stretched elastic wrap member 1830 and the tightened elastic portion 1880 of the shoe upper 1825 provides the wearer with a tight compression fit. In addition, because the relatively thick elastic portion 1880 of the shoe upper closely adheres to the foot of the wearer, the wearer is also provided with a feeling of additional support and soft flexible bulk than would be felt if only the elastic wrap member 1830 were closely adhered to the foot of the wearer.

Article of Footwear with Flexible Braces in Upper

FIGS. 19A-19F depict another alternative embodiment of an article of footwear 1910 including a sole 1915 connected to a shoe upper 1925 and two brace members 1930. In this embodiment, the sole 1915 is provided as a cleat, and the shoe upper 1925 is provided in the form of an athletic boot. The two brace members 1930 include a lateral brace member 1932 and a medial brace member 1934.

As best shown in FIGS. 19A and 19D-19F, each brace member 1930 includes a base portion 1940, a central shaft portion 1950 (which may also be referred to herein as a stem 1950), and a top plate 1960, which together form a single integral component (i.e., a unitary component with inseparable sections that are integrally formed). The brace members 1930 may be formed using any of various conventional manufacturing methods, such as injection molding. Each brace member 1930 is comprised of a relatively hard and non-elastic, yet resilient material, such as nylon, or other polymer material. As explained in further detail below, this material allows each brace member 1930 to provide support to the foot 1999 of the wearer, deform when a substantial force is applied to the brace member, and then resiliently return to the original shape when the force is removed.

The base portion 1940 of the brace member 1930 is a plate-like structure with a triangular shape. A flange 1942 is provided near the bottom of the base portion 1940. The flange 1942 is configured to fit under the insole of the article of footwear 1910 to provide a foundation for the brace member 1930. The base portion 1940 extends upward from the flange 1942 to an apex 1944. As best shown in FIG. 19A, the apex 1944 is located at a position above the heel and below the ankle on the foot 1999 of the wearer. An inner face 1946 and an opposing outer face 1948 are defined between the flange 1942 and the apex 1944. The apex 1944 of the base portion 1940 feeds into and merges with the stem 1950.

The stem 1950 of the brace member 1930 is a curved rod-like structure that begins at the apex 1944 of the base portion 1940 and extends rearward and upward toward a dorsal inflection point 1952 located to the rear of the ankle of the wearer. From this inflection point 1952, the stem 1950 extends forward and upward until it feeds into the top plate 1960. Accordingly, the stem 1940 provides a C-shaped rod that curves around the rear of the ankle of the wearer. The stem 1950 is wider at the inflection point 1952 than at other locations on the brace. Thus, as measured in the lateral direction of the foot 1999, the brace member 1930 is widest at the inflection point 1952 of the stem 1950, and gradually tapers upward and downward from the inflection point 1952 to the thinnest areas that merge with the base 1940 and the top plate 1960. While the brace member 1930 is widest in the lateral direction at this inflection point 1952, it will be recognized that the brace member 1930 is deeper at the base 1940 and the top plate 1960 than at the stem 1950 (i.e., the brace 1930 has a greater length in the direction from toe to heel of the foot 1999 at the base 1940 and top plate 1960 than at the stem 1950). As explained in further detail below, this configuration allows the brace member 1930 to bend/pivot in a forward direction (as indicated by arrow 1933 of FIGS. 19A and 19D) about the inflection point 1952.

The top plate 1960 of the brace member 1930 is triangular in shape and includes a curved upper edge 1962, an inner face 1966, and an opposite outer face 1968. The inner face 1966 provides a generally flat support surface that faces the lower leg/foot of the wearer and provides support to the lower leg/foot of the wearer when lateral forces act against the top plate 1960.

Figure 19B:
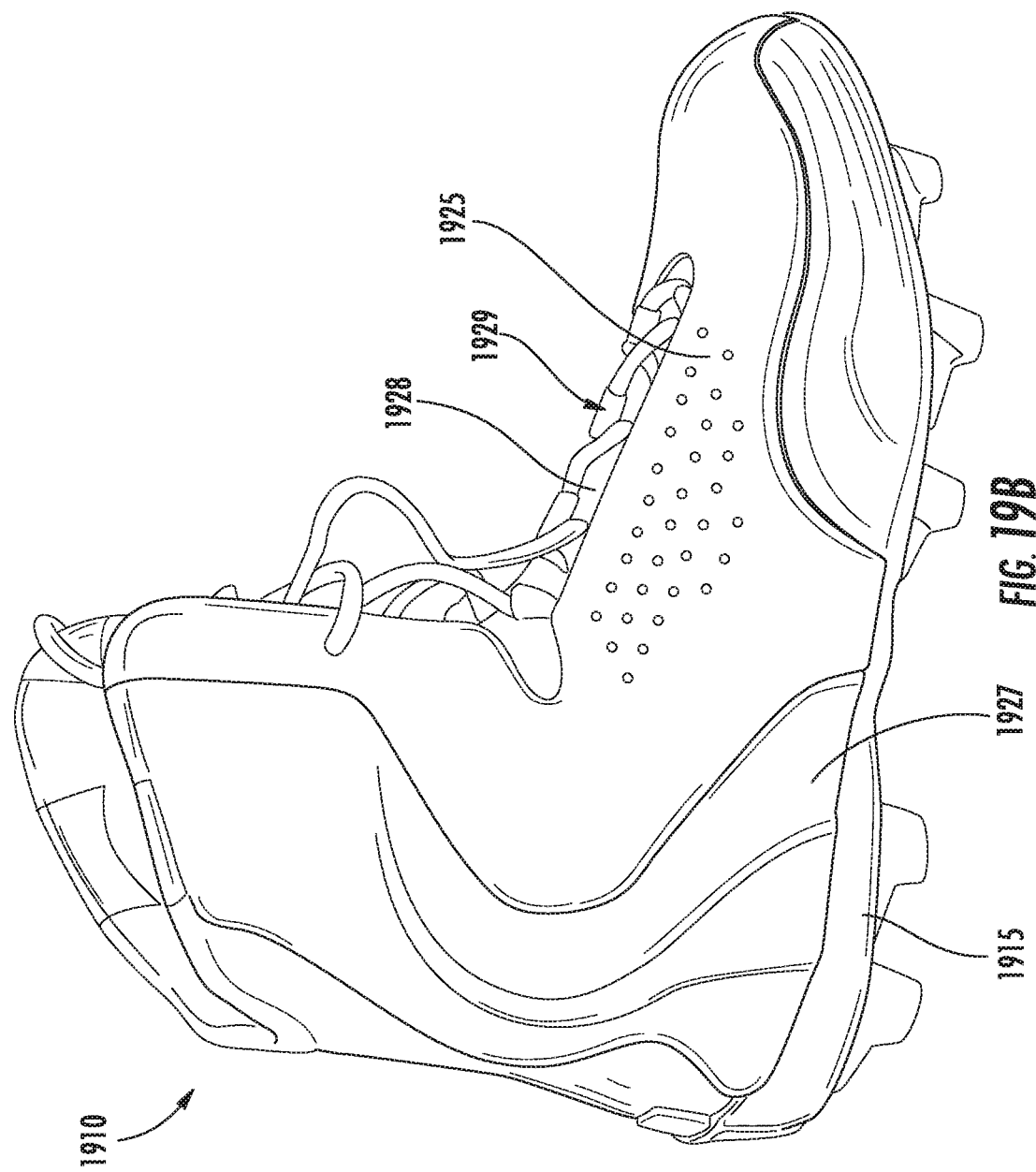
FIG. 19B shows a side view of the article of footwear of FIG. 19A.
Figure 19D:
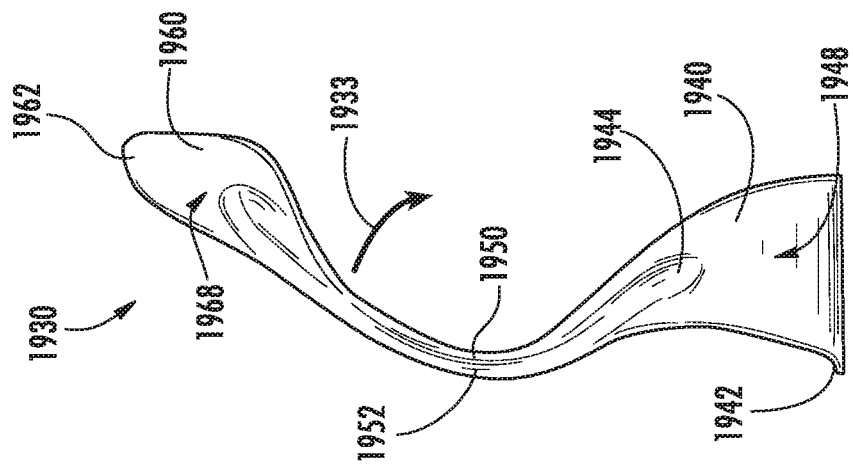
FIG. 19D shows a view of an outer face of the support brace of FIG. 19A.
Figure 19C:
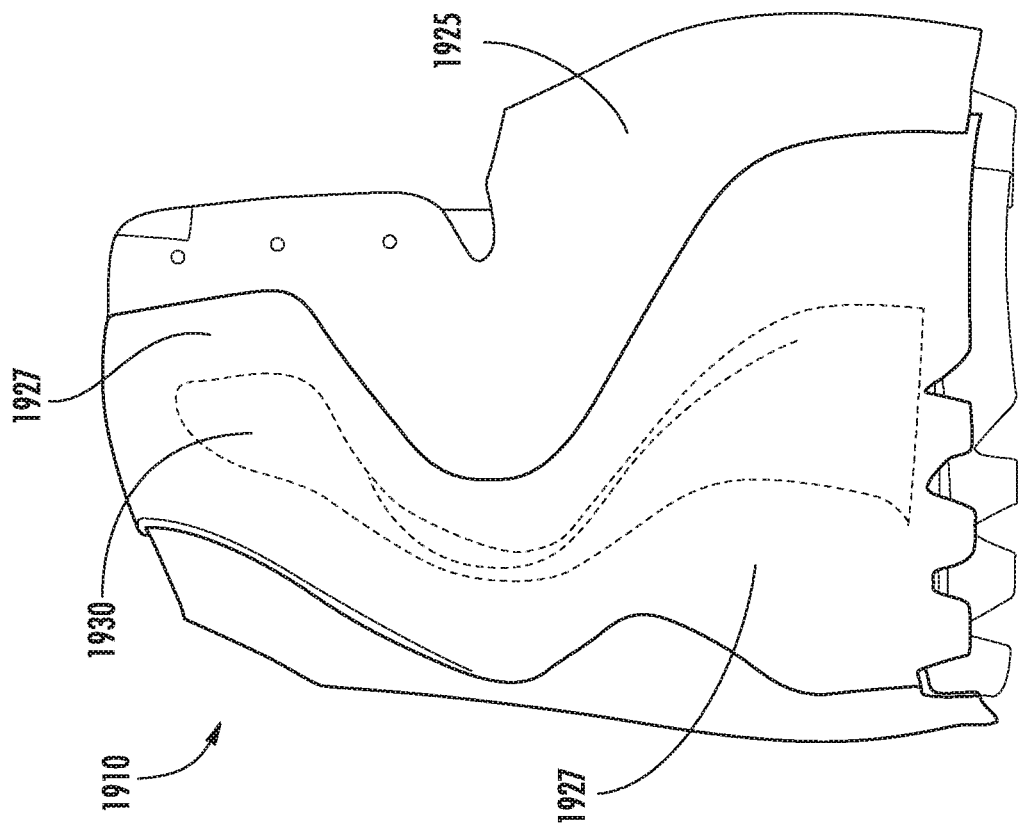
FIG. 19C shows a view of a pocket in the shoe upper carrying the support brace of FIG. 19A.

With reference now to FIGS. 19B and 19C, the brace members 1930 are configured to fit within closed pockets 1927 in the shoe upper 1925 (see FIGS. 19B and 19C). The pockets 1927 are not open to the foot cavity or the exterior of the article of footwear 1910. Accordingly, the brace members 1930 are embedded between an interior and exterior layers of the shoe upper 1925 where the pockets 1927 are formed. FIG. 19B shows the shoe upper 1925 with the exterior layer 1929 that forms the outside of one of the pockets 1927. FIG. 19C shows the exterior layer 1929 as transparent such that the pocket 1927 is exposed with the brace member 1930 in the pocket. Because the brace members 1930 are completely enclosed within the pockets 1927, the foot 1999 of the wearer is not in direct contact with the brace members 1930. Additionally, the inner walls of the foot cavity may include padding along the pockets 1927 to cushion the foot of the wearer from the relatively hard brace members 1930.

With reference again to FIG. 19A, in an alternative embodiment, the article of footwear 1910 may include support belts 1970. The support belts 1970 are positioned within the support cavity and are comprised of a generally inelastic woven material, such as a woven polyester or nylon material. One end 1972 of each support belt 1970 is fastened to the top plate 1960 and an opposite end 1974 of the support belt 1970 is coupled to some portion of the upper 1925, such as the eyelets 1928 of the article of footwear 1910. A slot (not shown) may be formed on the inner layer of the shoe upper 1925 that allows the support belt 1970 to extend through the inner layer of the shoe upper and be fastened to the top plate 1960 of the brace member 1930. The support belt 1970 may be fastened to the top plate 1960 using any of various means fastening means, such as adhesives, welding or mechanical fasteners (e.g., rivets, screws, etc.). As shown in FIG. 19A, the support belts 1970 generally extend downward from the top plate 1960 as a narrow strip of material, under the insole (and thus under the foot 1999), and back to a perimeter of the tongue slot 1929 (e.g., to the eyelets 1928). Thus, one end of each support belt 1970 is positioned on the lateral side of the article of footwear 1910, and the opposite side of the support belt is positioned on the medial side of the article of footwear 1910.

In operation, the brace members 1930 prevent unnatural lateral twisting of the ankle, but allow for natural forward pivoting of the ankle (such as that experienced during walking or running). In particular, the C-shaped structure of the stem 1950 allows the brace member 1930 to easily bend forward in the direction of arrow 1933 (see FIGS. 19A and 19D), when the wearer walks or runs. This forward bending action is primarily experienced at the inflection point 1952, which is the point at which the brace member 1930 is designed to bend. After bending forward, the resilient nature of the brace member 1930 allows the stem 1950 to return to its equilibrium position, as shown in FIG. 19A. Thus, the brace member 1930 has very little impact on the foot 1999 of the wearer during natural running or walking motions.

On the other hand, when the wearer experiences an unnatural twisting of the ankle (causing the brace member 1930 to experience forces in the direction of arrow 1935 of FIG. 19A), the brace member 1930 provides support to the foot of the wearer and helps prevent extreme twisting of the ankle. In particular, when the ankle begins to twist in a lateral or medial direction, the leg of the wearer presses against the top plate 1960. However, the brace member 1930 is not designed to easily bend in the lateral or medial direction. Instead, the brace member 1930 is only designed to easily bend in a forward direction 1933 at the inflection point 1952. The width and shape of the brace member 1930 at the inflection point 1952 means that the brace member 1930 significantly resists lateral bending (in the direction of arrow 1935). This results in an opposing force against the leg of the wearer when the ankle begins to twist. If this opposing force is strong enough, the wearer may avoid or reduce the severity of an ankle sprain from lateral or medial twisting of the ankle.

Although the present invention has been described with respect to certain preferred embodiments, it will be appreciated by those of skill in the art that other implementations and adaptations are possible. Moreover, there are advantages to individual advancements described herein that may be obtained without incorporating other aspects described above. Therefore, the spirit and scope of any appended claims should not be limited to the description of the preferred embodiments contained herein.

What is claimed is:

1. A cleated article of footwear comprising:
   a sole including a cleat;
   an upper coupled to the sole to form a foot cavity configured to receive a foot of a person wearing the cleated article of footwear, wherein the upper defines an outer surface, an inner surface, a forefoot region, a midfoot region oriented rearward of the forefoot region, a tongue slot, an ankle region oriented rearward of the forefoot region, a lateral side and a medial side;

a plurality of side-by-side tensioning straps positioned inside the foot cavity and movably coupled to the upper, the tensioning straps being present within the midfoot region of the upper, each of the tensioning straps including a first end attached to a lower lateral side inside the foot cavity and engaging the inner surface of the upper, a second end positioned outside the foot cavity on the medial side of the upper and engaging the outer surface of the upper, and a middle portion extending between the first end and the second end and across the tongue slot;

a plurality of side-by-side elongated channels positioned on the inner surface on the lateral side of the upper, each of the elongated channels designed and dimensioned such that said each elongated channel respectively encloses one of the tensioning straps with a width of each tensioning strap retained within a width of one of the elongated channels and extending from a first open end to a second open end of said elongated channel; and an adjustment tab in contact with the second end of each of the tensioning straps and disposed rearward of the midfoot region on the outer surface of the upper, the adjustment tab being moveable relative to the outer surface of the upper and operable to manipulate tension applied to the foot by the tensioning straps.

2. The cleated article of footwear according to claim 1, wherein the tensioning straps are configured to apply a selected compressive force to a midfoot region of the foot positioned inside the foot cavity.

3. The cleated article of footwear according to claim 1, wherein the adjustment tab maintains and locks applied tension of the tensioning straps.

4. The cleated article of footwear according to claim 3, wherein: the outer surface of the upper is provided on an outer shell and the inner surface of the upper is provided on an inner layer.

5. The cleated article of footwear according to claim 4, wherein each of the tensioning straps is attached to the inner layer such that the tensioning strap travels from the foot cavity, through an opening in the upper, and terminates outside of the outer shell.

6. The cleated article of footwear according to claim 1, wherein the tensioning straps are inelastic tensioning straps formed from an inelastic fabric material.

7. The cleated article of footwear according to claim 1, wherein: the tensioning straps are first tensioning straps; and the cleated article of footwear further comprises a plurality of second side-by-side tensioning straps that extend from the medial side to the lateral side of the article of footwear and crisscross the plurality of first tensioning straps.

8. The cleated article of footwear according to claim 1, wherein the channels are defined by a sleeve disposed upon the inner surface of the upper within the foot cavity.

9. The cleated article of footwear according to claim 1, wherein the tensioning straps are configured to apply compression to the foot positioned within the foot cavity.

10. The cleated article of footwear according to claim 1 wherein the adjustment tab is configured to lock the tensioning straps in place to apply continuing compressive force to the foot within the foot cavity.

11. An article of footwear comprising:
a sole;
an upper coupled to the sole to form a foot cavity configured to receive a foot of a person wearing the article of footwear, wherein the upper defines an outer surface, an inner surface, a forefoot region, a midfoot region oriented rearward of the forefoot region, an ankle region oriented rearward of the forefoot region, a tongue slot, a medial side and a lateral side;
a plurality of aligned elongated channels arranged on the inner surface on the lateral side of the upper;
a plurality of aligned tensioning straps inside the foot cavity and movably coupled to the upper, the tensioning straps being present within the midfoot region of the upper, each of the tensioning straps including a first end attached inside the foot cavity on a lower portion of the lateral side of the upper, a channel portion extending through and enclosed by a respective one of the elongated channels, a tongue portion extending across the tongue slot, and a second end positioned outside the foot cavity and engaging the outer surface of the upper on the medial side of the upper; and
an adjustment tab in contact with the second end of each tensioning strap and disposed in the ankle region on the outer surface of the upper, the adjustment tab being operable to manipulate tension applied to the foot by the tensioning straps.

12. The article of footwear of claim 11 wherein the adjustment tab is moveable relative to the outer surface of the upper.

13. The article of footwear of claim 11 wherein the tensioning straps are configured to apply a selected compressive force to a midfoot region of the foot positioned inside the foot cavity, and wherein the adjustment tab maintains and locks applied tension of the tensioning straps.

14. The article of footwear of claim 11 wherein the plurality of tensioning straps is a first plurality of tensioning straps, the article of footwear further comprising a second plurality of side-by-side tensioning straps extending from the medial side to the lateral side of the upper and crisscrossing the first plurality of tensioning straps.

15. An article of footwear comprising:
a sole;
an upper coupled to the sole to form a foot cavity configured to receive a foot of a person wearing the article of footwear, wherein the upper defines an outer surface, an inner surface, a forefoot region, a midfoot region oriented rearward of the forefoot region, an ankle region oriented rearward of the forefoot region, a tongue slot, a first side and a second side;
a plurality of side-by-side elongated channels positioned on the inner surface of the upper on the first side of the upper;
a plurality of side-by-side tensioning members inside the foot cavity and movably coupled to the upper, the tensioning members being present within the midfoot region of the upper, the tensioning members including a first end attached inside the foot cavity on a lower portion of the first side of the upper, a channel portion extending through and enclosed within a respective one of the elongated channels, a tongue portion extending across the tongue slot, and a second end positioned outside the foot cavity and engaging the outer surface on the second side of the upper; and
an adjustment member in contact with the second end of the tensioning members on the second side of the upper and moveable relative to the outer surface of the upper, the adjustment member being operable to manipulate tension applied to the foot by the tensioning members.

16. The article of footwear of claim 15 wherein the adjustment member is disposed rearward of the midfoot region.

17. The article of footwear of claim 15 wherein the tensioning members are configured to apply a selected compressive force to a midfoot region of the foot positioned inside the foot cavity, and wherein the adjustment member maintains and locks applied tension of the tensioning members.

18. The article of footwear of claim 15 wherein the plurality of tensioning members is a first plurality of tensioning members, the article of footwear further comprising a second plurality of side-by-side tensioning members extending from the second side to the first side of the upper and crisscrossing the first plurality of tensioning members.

* * * * *